(12) United States Patent
Brown et al.

(10) Patent No.: US 11,144,544 B2
(45) Date of Patent: *Oct. 12, 2021

(54) PROVIDING ANSWERS TO QUESTIONS INCLUDING ASSEMBLING ANSWERS FROM MULTIPLE DOCUMENT SEGMENTS

(71) Applicant: International Business Machines Corporation, Armonk, NY (US)

(72) Inventors: Eric W. Brown, New Fairfield, CT (US); Jennifer Chu-Carroll, Dobbs Ferry, NY (US); David A. Ferrucci, Yorktown Heights, NY (US); James W. Murdock, IV, Amawalk, NY (US)

(73) Assignee: International Business Machines Corporation, Armonk, NY (US)

( * ) Notice: Subject to any disclaimer, the term of this patent is extended or adjusted under 35 U.S.C. 154(b) by 261 days.

This patent is subject to a terminal disclaimer.

(21) Appl. No.: 16/411,828

(22) Filed: May 14, 2019

(65) Prior Publication Data

US 2019/0266157 A1    Aug. 29, 2019

Related U.S. Application Data

(63) Continuation of application No. 15/966,191, filed on Apr. 30, 2018, now Pat. No. 10,331,663, which is a
(Continued)

(51) Int. Cl.
*G06F 16/2452* (2019.01)
*G06F 3/048* (2013.01)
(Continued)

(52) U.S. Cl.
CPC .......... *G06F 16/24522* (2019.01); *A61B 5/00* (2013.01); *A61B 34/10* (2016.02);
(Continued)

(58) Field of Classification Search
None
See application file for complete search history.

(56) References Cited

U.S. PATENT DOCUMENTS 3,559,995 A    2/1971 Steadman
4,594,686 A    6/1986 Yoshida
(Continued)

FOREIGN PATENT DOCUMENTS

CN    1822630 A    8/2006
CN    1826597 A    8/2006
(Continued)

OTHER PUBLICATIONS

Chu-Carroll et al., "In Question-Ansering, Two Heads are Better than One", HLT-NAACL'03, May-Jun. 2003, pp. 24-31, Edmonton, Canada.
(Continued)

*Primary Examiner* — Thu N Nguyen
(74) *Attorney, Agent, or Firm* — Scully, Scott, Murphy & Presser, P.C.; Brian Welle, Esq.

(57) ABSTRACT

A method, system and computer program product for generating answers to questions. In one embodiment, the method comprises receiving an input query, identifying a plurality of candidate answers to the query; and for at least one of these candidate answers, identifying at least one proof of the answer. This proof includes a series of premises, and a multitude of documents are identified that include references to the premises. A set of these documents is selected that include references to all of the premises. This set of documents is used to generate one or more scores for the one of the candidate answers. A defined procedure is applied to the candidate answers to determine a ranking for the answers, and this includes using the one or more scores for the at least one of the candidate answers in the defined
(Continued)

procedure to determine the ranking for this one candidate answer.

20 Claims, 7 Drawing Sheets

Related U.S. Application Data continuation of application No. 15/432,449, filed on Feb. 14, 2017, now Pat. No. 9,965,509, which is a continuation of application No. 15/348,431, filed on Nov. 10, 2016, now Pat. No. 9,864,818, which is a continuation of application No. 13/618,131, filed on Sep. 14, 2012, now Pat. No. 9,495,481, which is a continuation of application No. 13/244,350, filed on Sep. 24, 2011, now Pat. No. 9,600,601.

(60) Provisional application No. 61/386,051, filed on Sep. 24, 2010.

(51) Int. Cl.

| | | |
|---|---|---|
| *G06N 5/02* | (2006.01) | |
| *G16H 50/70* | (2018.01) | |
| *G16H 10/20* | (2018.01) | |
| *G16H 50/20* | (2018.01) | |
| *G06F 16/31* | (2019.01) | |
| *G06F 16/93* | (2019.01) | |
| *G06F 16/33* | (2019.01) | |
| *G06F 16/532* | (2019.01) | |
| *G06F 16/242* | (2019.01) | |
| *G06F 16/2455* | (2019.01) | |
| *G06F 16/903* | (2019.01) | |
| *A61B 5/00* | (2006.01) | |
| *G06F 40/134* | (2020.01) | |
| *G06F 40/169* | (2020.01) | |
| *A61B 34/10* | (2016.01) | |
| *G16H 70/00* | (2018.01) | |
| *G16H 10/60* | (2018.01) | |
| *G16H 15/00* | (2018.01) | |
| *G16H 40/20* | (2018.01) | |
| *G06F 40/211* | (2020.01) | |

(52) U.S. Cl.
CPC .......... *G06F 3/048* (2013.01); *G06F 16/2428* (2019.01); *G06F 16/2455* (2019.01); *G06F 16/31* (2019.01); *G06F 16/334* (2019.01); *G06F 16/532* (2019.01); *G06F 16/90335* (2019.01); *G06F 16/93* (2019.01); *G06F 40/134* (2020.01); *G06F 40/169* (2020.01); *G06N 5/027* (2013.01); *G16H 10/20* (2018.01); *G16H 10/60* (2018.01); *G16H 15/00* (2018.01); *G16H 40/20* (2018.01); *G16H 50/20* (2018.01); *G16H 50/70* (2018.01); *G16H 70/00* (2018.01); *G06F 40/211* (2020.01); *Y02A 90/10* (2018.01)

(56) References Cited

U.S. PATENT DOCUMENTS

| | | | |
|---|---|---|---|
| 4,599,691 A | 7/1986 | Sakaki et al. | |
| 4,829,423 A | 5/1989 | Tennant et al. | |
| 4,921,427 A | 5/1990 | Dunn | |
| 5,374,894 A | 12/1994 | Fong | |
| 5,414,797 A | 5/1995 | Vassiliadis et al. | |
| 5,513,116 A | 4/1996 | Buckley et al. | |
| 5,546,316 A | 8/1996 | Buckley et al. | |
| 5,550,746 A | 8/1996 | Jacobs | |
| 5,559,714 A | 9/1996 | Banks et al. | |
| 5,634,051 A | 5/1997 | Thomson | |
| 5,794,050 A | 8/1998 | Dahlgren et al. | |
| 6,487,545 B1 | 11/2002 | Wical | |
| 6,665,666 B1 | 12/2003 | Brown et al. | |
| 6,763,341 B2 | 7/2004 | Okude | |
| 6,829,603 B1 | 12/2004 | Chai et al. | |
| 6,947,885 B2 | 9/2005 | Bangalore et al. | |
| 6,983,252 B2 | 1/2006 | Matheson et al. | |
| 7,092,928 B1 | 8/2006 | Elad et al. | |
| 7,136,909 B2 | 11/2006 | Balasuriya | |
| 7,139,752 B2 | 11/2006 | Broder et al. | |
| 7,181,438 B1 | 2/2007 | Szabo | |
| 7,197,497 B2 | 5/2007 | Cossock | |
| 7,216,073 B2 | 5/2007 | Lavi et al. | |
| 7,313,515 B2 | 12/2007 | Crouch et al. | |
| 7,558,778 B2 | 7/2009 | Carus et al. | |
| 7,590,606 B1 | 9/2009 | Keller et al. | |
| 7,730,085 B2 | 6/2010 | Hassan et al. | |
| 7,805,303 B2 | 9/2010 | Sugihara et al. | |
| 7,826,965 B2 | 11/2010 | Sadri et al. | |
| 8,032,483 B1 | 10/2011 | Haveliwala et al. | |
| 8,694,535 B2 | 4/2014 | Oleynik | |
| 2001/0032211 A1 | 10/2001 | Kuzumaki | |
| 2002/0188586 A1 | 12/2002 | Veale | |
| 2003/0033287 A1 | 2/2003 | Shanahan et al. | |
| 2004/0049499 A1 | 3/2004 | Nomoto et al. | |
| 2004/0064305 A1 | 4/2004 | Sakai | |
| 2004/0122660 A1 | 6/2004 | Cheng et al. | |
| 2004/0254917 A1 | 12/2004 | Brill et al. | |
| 2005/0033711 A1 | 2/2005 | Horvitz et al. | |
| 2005/0060301 A1 | 3/2005 | Seki et al. | |
| 2005/0086045 A1 | 4/2005 | Murata | |
| 2005/0086222 A1 | 4/2005 | Wang et al. | |
| 2005/0114327 A1 | 5/2005 | Kumamoto et al. | |
| 2005/0143999 A1 | 6/2005 | Ichimura | |
| 2005/0256700 A1 | 11/2005 | Moldovan et al. | |
| 2005/0289168 A1 | 12/2005 | Green et al. | |
| 2006/0053000 A1 | 3/2006 | Moldovan et al. | |
| 2006/0106788 A1 | 5/2006 | Forrest | |
| 2006/0122834 A1 | 6/2006 | Bennett | |
| 2006/0141438 A1 | 6/2006 | Chang et al. | |
| 2006/0160054 A1 | 7/2006 | Onishi et al. | |
| 2006/0173834 A1 | 8/2006 | Brill et al. | |
| 2006/0204945 A1 | 9/2006 | Masuichi et al. | |
| 2006/0206472 A1 | 9/2006 | Masuichi et al. | |
| 2006/0206481 A1 | 9/2006 | Ohkuma et al. | |
| 2006/0235689 A1 | 10/2006 | Sugihara et al. | |
| 2006/0277165 A1 | 12/2006 | Yoshimura et al. | |
| 2006/0282414 A1 | 12/2006 | Sugihara et al. | |
| 2006/0294037 A1 | 12/2006 | Horvitz et al. | |
| 2007/0022099 A1 | 1/2007 | Yoshimura et al. | |
| 2007/0022109 A1 | 1/2007 | Imielinski et al. | |
| 2007/0061703 A1 | 3/2007 | Kambhatla et al. | |
| 2007/0073533 A1 | 3/2007 | Thione et al. | |
| 2007/0073683 A1 | 3/2007 | Kobayashi et al. | |
| 2007/0078842 A1 | 4/2007 | Zola et al. | |
| 2007/0094285 A1 | 4/2007 | Agichtein et al. | |
| 2007/0118518 A1 | 5/2007 | Wu et al. | |
| 2007/0136246 A1 | 6/2007 | Stenchikova et al. | |
| 2007/0196804 A1 | 8/2007 | Yoshimura et al. | |
| 2007/0203863 A1 | 8/2007 | Gupta et al. | |
| 2007/0255555 A1 | 11/2007 | Crouch et al. | |
| 2008/0077570 A1 | 3/2008 | Tang et al. | |
| 2008/0189263 A1 | 8/2008 | Nagle | |
| 2009/0083262 A1 | 3/2009 | Chang et al. | |
| 2009/0192966 A1 | 7/2009 | Horvitz et al. | |
| 2009/0259642 A1 | 10/2009 | Cao et al. | |
| 2009/0287678 A1 | 11/2009 | Brown et al. | |
| 2009/0292687 A1 | 11/2009 | Fan et al. | |
| 2010/0100546 A1 | 4/2010 | Kohler | |

(56) References Cited

U.S. PATENT DOCUMENTS

2011/0066587 A1     3/2011   Ferrucci et al.
2018/0107793 A1*   4/2018   Ni .......................... G16H 10/60

FOREIGN PATENT DOCUMENTS

| CN | 1916898 A | 2/2007 |
|---|---|---|
| CN | 101377777 A | 3/2009 |

OTHER PUBLICATIONS

Ferrucci et al., "Towards the Open Advancement of Question Answering Systems," IBM Technical Report RC24789, Computer Science, Apr. 22, 2009.
Moldovan et al., "COGEX: A Logic Prover for Question Answering," Proceedings of HLT-NAACL 2003, May-Jun. 2003, pp. 87-93, Edmonton, Canada.
Simmons, "Natural Language Question-Answering Systems: 1969," Communications of the ACM, Jan. 1970, pp. 15-30, 13(1).
Voorhees et al., "Overview of the TREC 2005 Question Answering Track," Proceedings of the Fourteenth Text Retrieval Conference, 2005, Gaithersburg, Maryland.
Weinstein et al., "Agents Swarming in Semantic Spaces to Corroborate Hypotheses," AAMAS'04, Jul. 19-23, 2004, New York, New York, USA, Copyright 2004 ACM 1-58113-864-4/04/007.
Prager et al., "A Multi-Strategy, Multi-Question Approach to Question Answering," In New Directions in Question-Answering, Maybury, M. (Ed ), AAAI Press, 2004.
Strzalkowski et al., "Advances in Open-Domain Question-Answering," Springer, 2006 (background information only—copy of the front cover, copyright page and table of contents only).
Balahur, "Going Beyond Traditional QA Systems: Challenges and Keys in Opinions Question Answering," Coling 2010: Poster Volume, pp. 27-35, Beijing, Aug. 2010.
Blitzer, Domain Adaptation of Natural Language Processing Systems, Presented to the Faculties of the University of Pennsylvania in Partial Fulfillment of the Requirements for the Degree of Doctor of Philosophy, 2007.
University of Illinois at Urbana-Champaign, Department of Computer Science, Research, 2010, http://cs.illinois.edu/research?report=UIUCDCS-R-2008-2974.
National Center for Biotechnology Information (NCBI), Entrez the Life Sciences Search Engine, Oct. 28, 2009.
Chang et al., "Creating An Online Dictionary of Abbreviations from MEDLINE," J Am Med Inform Assoc. 2002; 9:612-620. DOI 10.1197/jamia.M1139.
Adar, "SaRAD: a Simple and Robust Abbreviation Dictionary," BIOINFORMATICS, Mar. 2004, pp. 527-533, vol. 20 Issue 4.
Cunningham et al., "The GATE User Guide", http://gate.ac.uk/releases/gate-2.0alpha2-build484/doc/userguide.html, This version of the document is for GATE version 2 alpha 1, of Mar. 2001, pp. 1-13.
"INDRI Language modeling meets inference networks," http://www.lemurproject.org/indri/, last modified May 23, 2011; pp. 1-2.
"Apache UIMA ConceptMapper Annotator Documentation," Written and maintained by the Apache UIMA Development Community, Version 2.3.1, Copyright 2006, 2011 The Apache Software Foundation, pp. 1-7, http://uima.apache.org/sandbox.html#concept.mapper.annotator.
"Question answering," From Wikipedia, the free encyclopedia, http://en.wikipedia.org/wiki/Question_answering, last modified Sep. 8, 2011.
Aditya et al., "Leveraging Community-built Knowledge for Type Coercion in Question Answering," Proceedings of ISWC 2011.
Pasca, "Question-Driven Semantic Filters for Answer Retrieval", International Journal of Pattern Recognition and Artificial Intelligence (IJPRAI), World Scientific Publishing, SI, vol. 17, No. 5, Aug. 1, 2003, pp. 741-756.
Cucerzan et al., "Factoid Question Answering over Unstructured and Structured Web Content", In Proceedings of the 14th Text Retrieval Conference TREC 2005, Dec. 31, 2005.
Molla et al., "AnswerFinder at TREC 2004", Proceedings of the 13th Text Retrieval Conference TREC 2004, Dec. 31, 2004.
23. Wikipedia, List of poets, Sep. 19, 2011, http://en.wikipedia.org/wiki/List_of_poets.
24. Delicious, The freshest bookmarks that are flying like hotcakes on Delicious and beyond, Sep. 21, 2011, http://delicious.com/.
25. Wikipedia, List of poets from the United States, Sep. 19, 2011, http://en.wikipedia.org/wiki/List_of_poets_from_the_United_States.

* cited by examiner

PROVIDING ANSWERS TO QUESTIONS INCLUDING ASSEMBLING ANSWERS FROM MULTIPLE DOCUMENT SEGMENTS

CROSS REFERENCE TO RELATED APPLICATIONS

This application is a continuation of copending U.S. patent application Ser. No. 15/966,191, filed Apr. 30, 2018, which is a continuation of U.S. patent application Ser. No. 15/432,449, filed Feb. 14, 2017, which is a continuation of U.S. patent application Ser. No. 15/348,431, filed Nov. 10, 2016, which is a continuation of U.S. patent application Ser. No. 13/618,131, filed Sep. 14, 2012, which is a continuation of U.S. patent application Ser. No. 13/244,350, filed Sep. 24, 2011. The entire contents and disclosure of U.S. patent application Ser. Nos. 15/966,191, 15/432,449, 15/348,431, 13/618,131 and 13/244,350 are hereby incorporated herein by reference in their entirety.

This application claims the benefit of the filing date of U.S. provisional patent application No. 61/386,051, filed Sep. 24, 2010, the disclosure of which is hereby incorporated by reference herein in its entirety.

BACKGROUND

This invention generally relates to information retrieval, and more specifically, to assembling answers from multiple documents. Even more specifically, embodiments of the invention relate to Question Answering systems and methods implementing parallel analysis for providing answers to questions and in which candidate answers may be assembled from multiple documents.

Generally, question answering (QA) is a type of information retrieval. Given a collection of documents (such as the World Wide Web or a local collection), a QA system should be able to retrieve answers to questions posed in natural language. QA is regarded as requiring more complex natural language processing (NLP) techniques than other types of information retrieval such as document retrieval, and QA is sometimes regarded as the next step beyond search engines.

QA research attempts to deal with a wide range of question types including: fact, list, definition, how, why, hypothetical, semantically-constrained, and cross-lingual questions. Search collections vary from small local document collections, to internal organization documents, to compiled newswire reports, to the world wide web.

Closed-domain question answering deals with questions under a specific domain (for example, medicine or automotive maintenance), and can be seen as an easier task because NLP systems can exploit domain-specific knowledge frequently formalized in ontologies. Alternatively, closed-domain might refer to a situation where only a limited type of questions are accepted, such as questions asking for descriptive rather than procedural information. Open-domain question answering deals with questions about nearly everything, and can only rely on general ontologies and world knowledge. Open-domain Q/A systems, though, usually have much more data available from which to extract the answer.

Access to information is currently dominated by two paradigms: a database query that answers questions about what is in a collection of structured records; and a search that delivers a collection of document links in response to a query against a collection of unstructured data (text, html etc.).

One major challenge in such information query paradigms is to provide a computer program capable of answering factual questions based on information included in a large collection of documents (of all kinds, structured and unstructured). Such questions can range from broad such as "what are the risk of vitamin K deficiency" to narrow such as "when and where was Hillary Clinton's father born".

User interaction with such a computer program could be either a single user-computer exchange or a multiple turn dialog between the user and the computer system. Such dialog can involve one or multiple modalities (text, voice, tactile, gesture etc.). Examples of such interaction include a situation where a cell phone user is asking a question using voice and is receiving an answer in a combination of voice, text and image (e.g. a map with a textual overlay and spoken (computer generated) explanation. Another example would be a user interacting with a video game and dismissing or accepting an answer using machine recognizable gestures or the computer generating tactile output to direct the user.

The challenge in building such a computer system is to understand the query, to find appropriate documents that might contain the answer, and to extract the correct answer to be delivered to the user. Currently, understanding the query is an open problem because computers do not have human ability to understand natural language nor do they have common sense to choose from many possible interpretations that current (very elementary) natural language understanding systems can produce.

Being able to answer a factual query in one or multiple dialog turns is of great potential value as it enables real time access to accurate information. For instance, advancing the state of the art in question answering has substantial business value, since it provides a real time view of the business, its competitors, economic conditions, etc. Even if QA is in a most elementary form, it can improve productivity of information workers by orders of magnitude.

U.S. patent application Ser. No. 12/152,441, the disclosure of which is hereby incorporated herein by reference in its entirety, describes a QA system involving the generation of candidate answers and selecting a final answer (or ranking a list of final answers) from among the set of candidate answers.

Current information retrieval and question answering systems attempt to satisfy a user's information need by identifying the single document segment (e.g., entire document, contiguous sequence of one or more sentences, or a single phrase) that is most likely to contain relevant information. There are many information needs, however, that cannot be satisfied by a single document segment.

SUMMARY OF THE INVENTION

Embodiments of the invention provide a method, system and computer program product for generating answers to questions. In one embodiment, the method comprises receiving an input query, conducting a search in one or more data sources to identify a plurality of candidate answers to the input query, and for at least one of the candidate answers, identifying at least one proof of the candidate answer, said proof including a series of premises for establishing said each proof. A multitude of documents are identified that include references to the premises, and a set of these documents, that as a set include references to all of the premises, is selected. This selected set of documents is used to generate one or more scores for said at least one of the candidate answers. In the method, a defined procedure is applied to the plurality of candidate answers to determine a ranking for each of the candidate answers, and this includes using said one or more scores for said at least one of the candidate answers in the defined procedure to determine the ranking for said at least one of the candidate answers.

In an embodiment, the set of documents is selected using a defined algorithm to identify a quasi-minimal set of documents.

In one embodiment, the set of documents is selected using a defined algorithm to identify a set of documents having the minimum number of documents needed to include references to all of the premises.

In an embodiment, each of the multitude of documents include references to a given number of the premises, and the documents are selected for the set in order of the number of the premises referenced in each of the documents.

In an embodiment, each of the multitude of documents include references to a given number of the premises, and the documents are selected for the set in order of the number of the premises referenced in each of the documents.

In one embodiment, the set of documents is selected based on the number of the premises referenced in each of the documents.

Embodiments of the invention provide a method and system for indexing documents. In an embodiment, the method comprises for each of the documents, annotating spans of text in said each document that refer to entities with entity types to form entity annotations, and annotating spans of text in said each document that refer to facts with fact types to form relation annotations. The method further comprises, for each of the annotated spans of text that refers to one of the facts, linking said one of the facts to said each annotation; and recording in an index the entities, the facts, the annotations that refer to said entities, and the annotations that refer to said facts.

In an embodiment, the method further comprises determining which of the entity annotations refer to the same fact, and determining which of the relation annotations refer to the same fact.

In one embodiment, the method further comprises using the index to identify a candidate answer for an input query. An embodiment further comprises using the facts and entities in the index to identify a proof for the candidate answer.

Embodiments of the invention provide a system and method for retrieving documents. In an embodiment, the system comprises a computer device comprising at least one distinct software module, each distinct software module being embodied on a tangible computer-readable medium; a memory; and at least one processor coupled to the memory. This processor is operative for searching through a given index to identify a candidate answer for an input query from a user, identifying at least one proof for the candidate answer, said proof including a series of premises, and searching through the index to identify a multitude of documents that include references to the premises of said one proof. A set of documents is selected that, as a set, include references to all of the premises, and this set is returned to the user.

In one embodiment, a defined algorithm is used to identify a quasi-minimal set of documents.

In an embodiment, a defined algorithm is used to identify a set of documents having the minimum number of documents needed to include references to all of the premises.

In an embodiment, each of the multitude of documents include references to a given number of the premises, and the set of documents are selected in order of the number of the premises referenced in each of the documents.

In an embodiment, the processor applies a defined algorithm to the sets of documents to identify one or more of the sets of documents as quasi-minimal sets of documents, and one or more of the quasi-minimal sets of documents is returned to the user.

BRIEF DESCRIPTION OF THE SEVERAL VIEWS OF THE DRAWINGS

The objects, features and advantages of the invention are understood within the context of the Description of Embodiments of the Invention, as set forth below. The Description of Embodiments of the Invention is understood within the context of the accompanying drawings, which form a material part of this disclosure, wherein.

DETAILED DESCRIPTION

As used herein, the words "question" and "query," and their extensions, are used interchangeably and refer to the same concept, namely a request for information. Such requests are typically expressed in an interrogative sentence, but they can also be expressed in other forms, for example as a declarative sentence providing a description of an entity of interest (where the request for the identification of the entity can be inferred from the context). "Structured information" (from "structured information sources") is defined herein as information whose intended meaning is unambiguous and explicitly represented in the structure or format of the data (e.g., a database table). "Unstructured information" (from "unstructured information sources") is defined herein as information whose intended meaning is only implied by its content (e.g., a natural language document). "Semi structured information" refers to data having some of its meaning explicitly represented in the format of the data, for example a portion of the document can be tagged as a "title".

Figure 1:
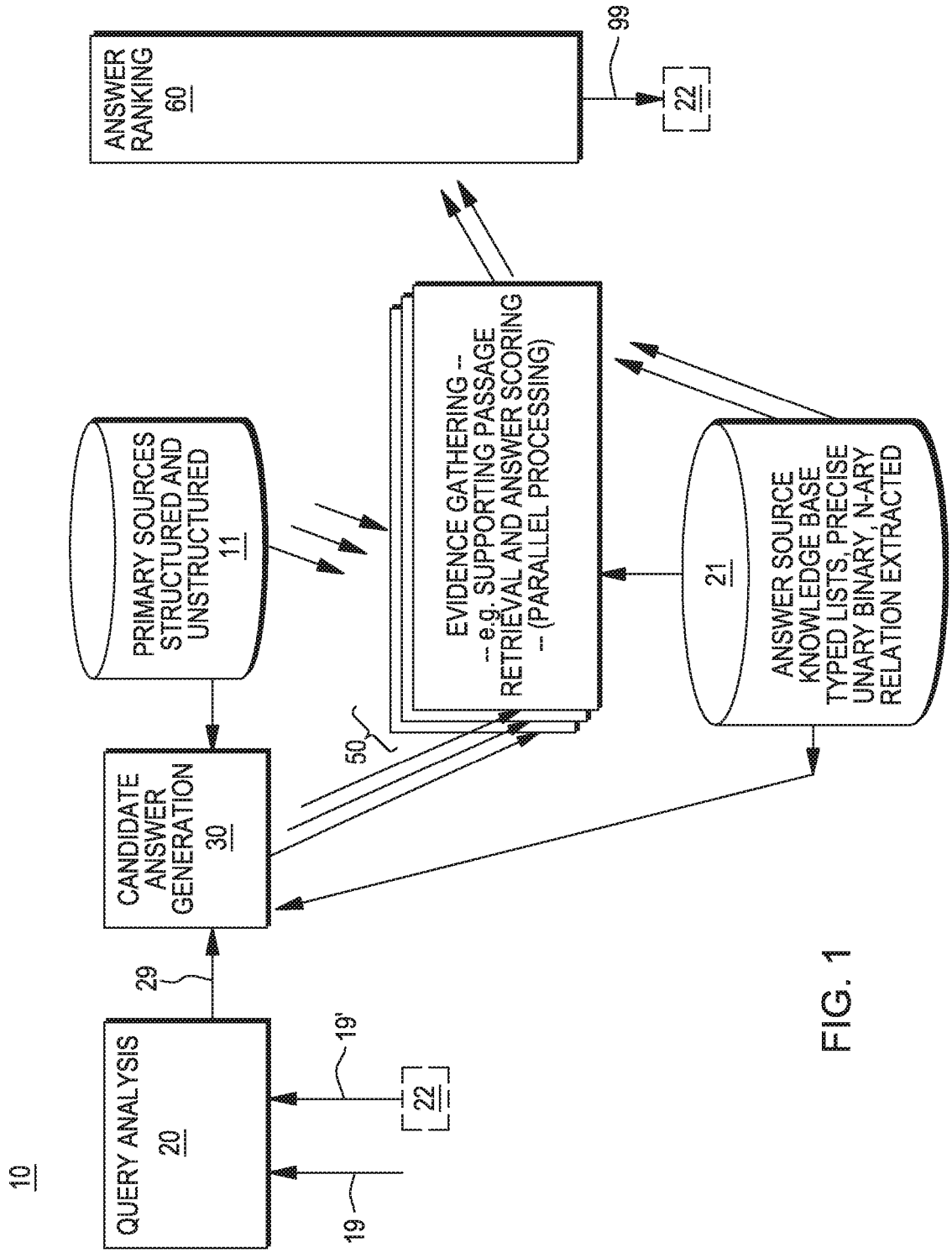
FIG. 1 shows a system diagram depicting a high level logical architecture and question/answering method for an embodiment of the present invention.

FIG. 1 shows a system diagram depicting a high-level logical architecture 10 and methodology of an embodiment of the present invention. As shown in FIG. 1, the architecture 10 includes a Query Analysis module 20 implementing functions for receiving and analyzing a user query or question. According to an embodiment of the invention, a "user" refers to a person or persons interacting with the system, and the term "user query" refers to a query (and its context) 19 posed by the user. However, it is understood other embodiments can be constructed, where the term "user" refers to a computer system 22 generating a query by mechanical means, and where the term "user query" refers to such a mechanically generated query and its context 19'. A candidate answer generation module 30 is provided to implement a search for candidate answers by traversing structured, semi structured and unstructured sources contained in a Primary Sources module 11 and in an Answer Source Knowledge Base module 21 containing collections of relations and lists extracted from primary sources. All the sources of information can be locally stored or distributed over a network, including the Internet. The Candidate Answer generation module 30 generates a plurality of output data structures containing candidate answers based upon the analysis of retrieved data. In FIG. 1, one embodiment is depicted that includes an Evidence Gathering module 50 interfacing with the primary sources 11 and knowledge base 21 for concurrently analyzing the evidence based on passages having candidate answers, and scoring each of the candidate answers as parallel processing operations.

Figure 2:
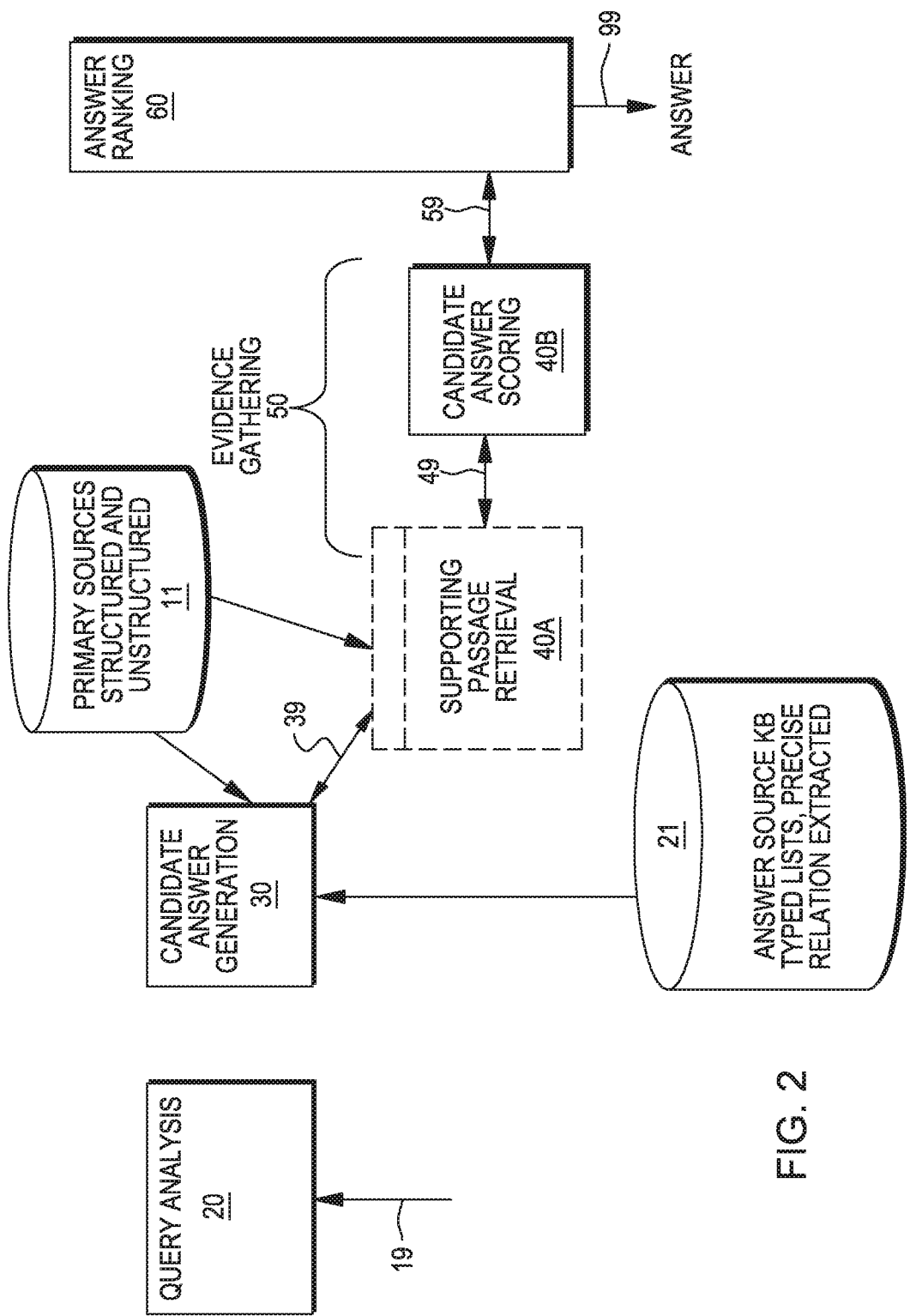
FIG. 2 shows a variant of the architecture of FIG. 1, where the Evidence Gathering module includes two submodules: Supporting Passage Retrieval and Candidate Answer Scoring.

In one embodiment, the architecture may be employed utilizing the Common Analysis System (CAS) candidate answer structures, and implementing Supporting Passage Retrieval as will be described in greater detail herein below. This processing is depicted in FIG. 2 where the Evidence Gathering module 50 comprises Supporting Passage Retrieval 40A and the Candidate Answer Scoring 40B as separate processing modules for concurrently analyzing the passages and scoring each of the candidate answers as parallel processing operations. The Answer Source Knowledge Base 21 may comprise one or more databases of structured or semi-structured sources (pre-computed or otherwise) comprising collections of relations (e.g., Typed Lists). In an example implementation, the Answer Source knowledge base may comprise a database stored in a memory storage system, e.g., a hard drive. An Answer Ranking module 60 provides functionality for ranking candidate answers and determining a response 99 that is returned to a user via a user's computer display interface (not shown) or a computer system 22. The response may be an answer, or an elaboration of a prior answer or a request for clarification in response to a question—when a high quality answer to the question is not found.

It is understood that skilled artisans may implement a further extension to the system shown in FIG. 1 to employ one or more modules for enabling I/O communication between a user or computer system and the system 10 according to, but not limited to, the modalities of text, audio, video, gesture, tactile input and output etc. Thus, in one embodiment, both an input query and a generated query response may be provided in accordance with one or more of multiple modalities including text, audio, image, video, tactile or gesture.

The processing depicted in FIGS. 1 and 2, may be local, on a server, or server cluster, within an enterprise, or alternately, may be distributed with or integral with or otherwise operate in conjunction with a public or privately available search engine in order to enhance the question answer functionality in the manner as described. Thus, embodiments of the invention may be provided as or provided in a computer program product comprising instructions executable by a processing device, or as a service deploying the computer program product. The architecture employs a search engine (a document retrieval system) as a part of a Candidate Answer Generation module 30 which may be dedicated to the Internet, a publicly available database, a web-site (e.g., IMDB.com), or a privately available database. Databases can be stored in any storage system, e.g., a hard drive or flash memory, and can be distributed over a network or not.

As mentioned, embodiments of the invention make use of the Common Analysis System (CAS), a subsystem of the Unstructured Information Management Architecture (UIMA), that handles data exchanges between the various UIMA components, such as analysis engines and unstructured information management applications. CAS supports data modeling via a type system independent of programming language, provides data access through a powerful indexing mechanism, and provides support for creating annotations on text data, such as described in (http://www.research.ibm.com/journal/sj/433/gotz.html) incorporated by reference as if set forth herein. CAS also allows for multiple definitions of the linkage between a document and its annotations, as is useful for the analysis of images, video, or other non-textual modalities.

In one embodiment, the UIMA may be provided as middleware for the effective management and interchange of unstructured information over a wide array of information sources. The architecture generally includes a search engine, data storage, analysis engines containing pipelined document annotators and various adapters. The UIMA system, method and computer program may be used to generate answers to input queries. The method includes inputting a document and operating at least one text analysis engine that comprises a plurality of coupled annotators for tokenizing document data and for identifying and annotating a particular type of semantic content. Thus it can be used to analyze a question and to extract entities as possible answers to a question from a collection of documents.

In one non-limiting embodiment, the Common Analysis System (CAS) data structure form is implemented as is described in U.S. Pat. No. 7,139,752, the whole contents and disclosure of which is incorporated by reference as if fully set forth herein.

Figure 3:
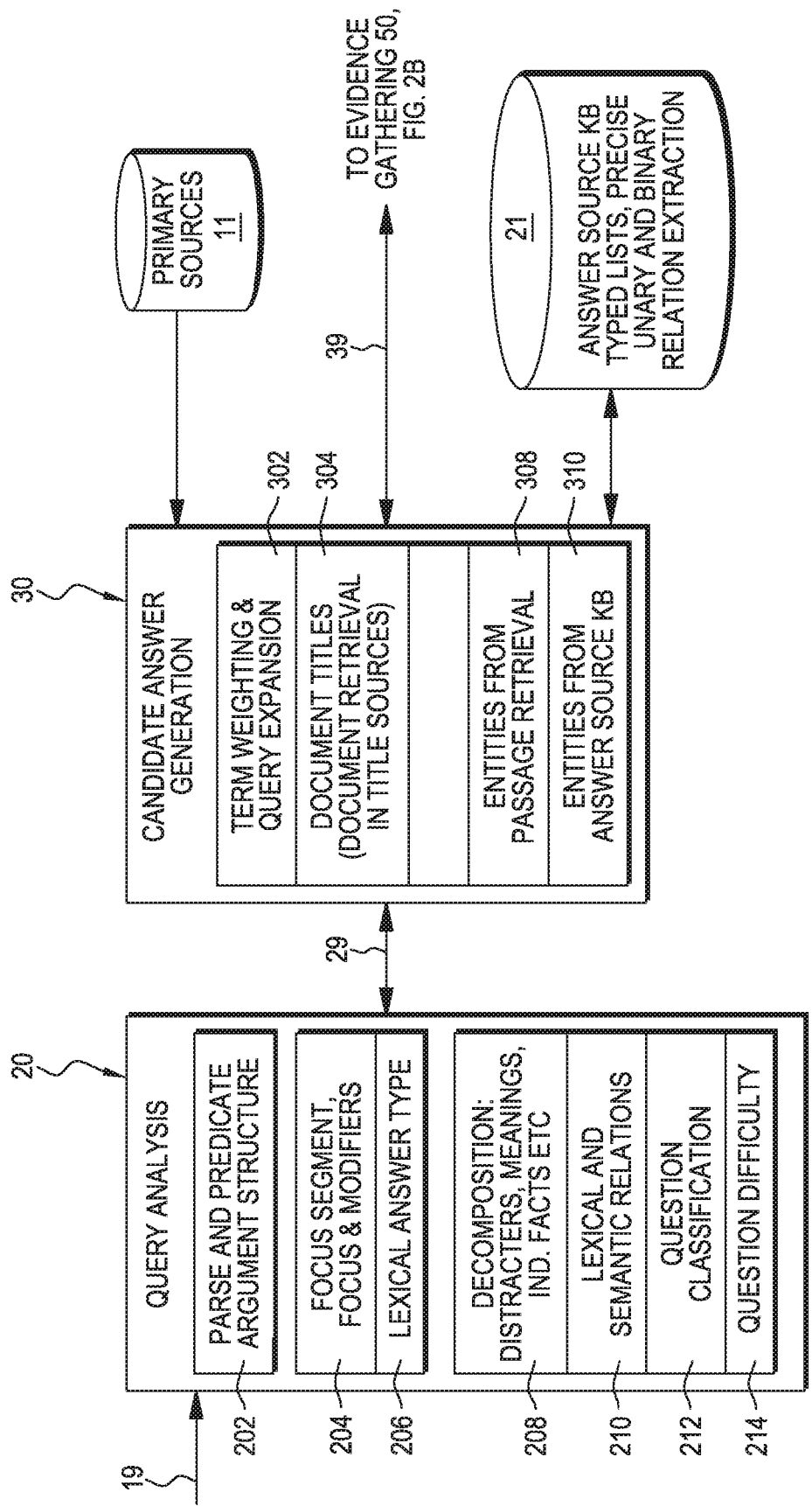
FIG. 3 shows a more detailed diagram of the Query Analysis and the Candidate Answer Generation modules of FIG. 1.

As shown in greater detail in the more detailed logical architecture diagram of FIG. 3, the "Query Analysis" module 20 receives an input that comprises the query 19 entered, for example, by a user via their web-based browser device. An input query 19 may comprise a string such as "Who was the tallest American president?". Alternately, a question may comprise of a string and an implicit context, e.g., "Who was the shortest?". In this example, context may range from a simple another string e.g. "American presidents" or ⵌho was the tallest American president??to any data structure, e.g. all intermediate results of processing of the previous strings—a situation arising e.g., in a multiple turn dialog. The input query is received by the Query Analysis module 20 which includes, but is not limited to, one or more the following sub-processes: Parse and Predicate Argument Structure block 202 a Focus Segment, Focus and Modifiers block 204; Lexical Answer Type block 206; Question Decomposition block 208; a Lexical and Semantic Relations module 210; a Question Classifier block 212; and a Question Difficulty module 214.

The Parse and Predicate Argument Structure block 202 implements functions and programming interfaces for decomposing an input query into its grammatical and semantic components, e.g., noun phrases, verb phrases and predicate/argument structure. An (English Slot Grammar) ESG-type parser may be used to implement block 202. The Focus Segment, Focus & Modifiers block 204 is provided to compute the focus and focus modifiers of the question, and is further described below. The Lexical Answer Type (LAT)

block 206 implements functions and programming interfaces to provide additional constraints on the answer type (Lexical) as will be described in greater detail herein below. The Question decomposition block 208 implements functions and programming interfaces for analyzing the input question to determine the sets of constraints specified by the question about the target answer. There are several ways that these constraints may relate to one another: 1) Nested Constraints; 2) Redundant Constraints; and 3) Triangulation. With nested constraints, an answer to an "inner" question instantiates an "outer" question. For example, "Which Florida city was named for the general who led the fight to take Florida from the Spanish?" With redundant constraints, one constraint uniquely identifies the answer. For instance, "This tallest mammal can run at 30 miles per hour. Which is it?". With triangulation, each constraint generates a set of answers and the correct answer is the one answer in common in the two (or more) sets. For example, in a "puzzle"-style question "What is a group of things of the same kind, or scenery constructed for a theatrical performance".

The Lexical and Semantic Relations module 210 is provided to detect lexical and semantic relations in the query (e.g., predicate-argument relations) as is the Question Classification block 212 that may employ topic classifiers providing information addressing, e.g., what is the question about? The Question Difficulty module 214 executes methods providing a way to ascertain a question's difficulty, e.g., by applying readability matrix to the question. It is understood that one or more of the query/question analysis processing blocks shown in FIG. 3 may be selected for a particular implementation.

The Parse and Predicate Arguments Structure block 202 implements functions and programming interfaces for decomposing an input query into its grammatical components by performing a Lexical processing and a syntactic and predicate argument structure analysis as known in the art. For an example query:

"In the 1960s this largest Kansas city became the world's largest producer of general aviation aircraft".

The Parse and Predicate Arguments block 202 will produce an example parse search results tree structure below, with e$\underline{X}$ providing an index into the tree, e.g., the "become" word is e8 (the $8^{th}$ structure of the results tree, and e7 indexes the $7^{th}$ word of the results tree structure) where 7 represents the word ("city") that is the first argument of "become" and e13 (indexes the $13^{th}$ word of the results tree structure) is the "producer" which is the second argument of "become" in the semantic structure depicted:

in(e1,e3,e8)
the(e2,e3)
1960s(e3,u)
this(e4,e7)
large(e5,e7)
Kansas(e6,e7)
city(e7,u)
become(e8,e7,e13)
the(e9,e10)
world(e10,u,e13)
aposts(e11,e10)
large(e12,e13)
producer(e13,of:e17)
general(e15,e17)
aviation(e16,u,e17)
aircraft(e17)

The Focus Segment, Focus and Modifiers block 204 detects a Focus Segment which is the text span in the question that the correct answer replaces. For example, in the following query, the italicized words represent the focus segment in the query:

"In the 1960s this largest Kansas city became the world's largest producer of general aviation aircraft."

To detect a focus segment, a set of rules that operate on Predicate-Argument structures and the ESG parse are implemented that match Patterns in Predicate-Argument Structure (PAS). Example patterns include, e.g., a Noun Phrase; "what/which/this/these X", where X is another object(s); "who/what/when/where/why/this/these"; a Pronoun without a referent. An example of a pronoun pattern with the pronoun words italicized is as follows:

As a boy he built a model windmill; his calculus foe Gottfried Leibniz designed them as an adult.

With reference to the Lexical Answer Type (LAT) block 206, LAT is the question terms that identify the semantic type of the correct answer. The italicized words in the following passage represent the LAT in the following query: "What Kansas city is the world's largest producer of general aviation aircraft".

LATs may include modifiers if they change the meaning. For example, the italicized words represent the LAT in the following query:

Joliet and Co found that the Mississippi emptied into what body of water?

Referring to FIG. 3, an output 29 of the Question/Query analysis block 20 comprises a query analysis result data structure (CAS structure). In this embodiment, the output data structure Question/Query analysis block 20 and the candidate answer generation block 30 may be implemented to pass the data among the modules, in accordance with the UIMA Open Source platform.

The "Candidate Answer Generation" module 30 receives the CAS-type query results data structure 29 output from the Question/Query analysis block 20, and generates a collection of candidate answers based on documents stored in Primary Sources 11 and in Answer Source KB 21. The "Candidate Answer Generation" module 30 includes, but is not limited to, one or more of the following functional sub-processing modules: A Term Weighting & Query Expansion module 302; a Document Titles (Document Retrieval in Title Sources) module 304; an Entities From Passage Retrieval module 308; and an Entities from Structural Sources K.B. module 310.

The Term Weighting and Query Expansion module 302 implements functions for creating a query against modules 11 and 21 (part of query generation) with an embodiment implementing query expansion (see, e.g., http://wikipedia.org/wiki/Query_expansion). The Document Titles (Document Retrieval in Title Sources) module 304 implements functions for detecting a candidate answer (from sources 11 and 21). The Entities From Passage Retrieval module 308 implements functions for detecting a candidate answer in textual passages, e.g. based on grammatical and semantic structures of the passages and the query. The Entities from Structured Sources module KB 310 implements functions for retrieving a candidate answer based on matches between the relations between the entities in the query and the entities in Answer Source KB 21, (implemented e.g. as an SQL query).

In embodiments of the invention, as a result of implementing the functional modules of the Candidate Answer Generation block 30, a query is created and run against all of the structured and unstructured primary data sources 11 in the (local or distributed) sources database or like memory storage device(s). This query may be run against the structured (KB), semi-structured (e.g., Wikipedia, IMDB databases, a collection of SEC filings in XBRL, etc.), or unstructured data (text repositories) to generate a candidate answer list 39 (also as a CAS, or an extension of prior CAS). It should be understood that, in one embodiment, the query is run against a local copy of the listed primary source databases, or may access the publically available public database sources. Moreover, it should be understood that, in one embodiment, not all the terms from the query need to be used for searching the answer—hence the need for creating the query based on results of the query analysis. For example, to answer the question Give letter previous capital of Poland?? the terms Give letter?should not be part of the query.

As further shown in FIG. 3, the Answer Source Knowledge Base 21 is shown interfacing with the Entities from Structured Sources module 310 that includes: Typed Lists (e.g., list of all countries in world), Precise Unary (e.g., a country), Binary (e.g., country+head of state of country), Ternary (e.g., country+head of state of country+wife of head of state), n-ary Relation Extracted, etc.

Figure 4:
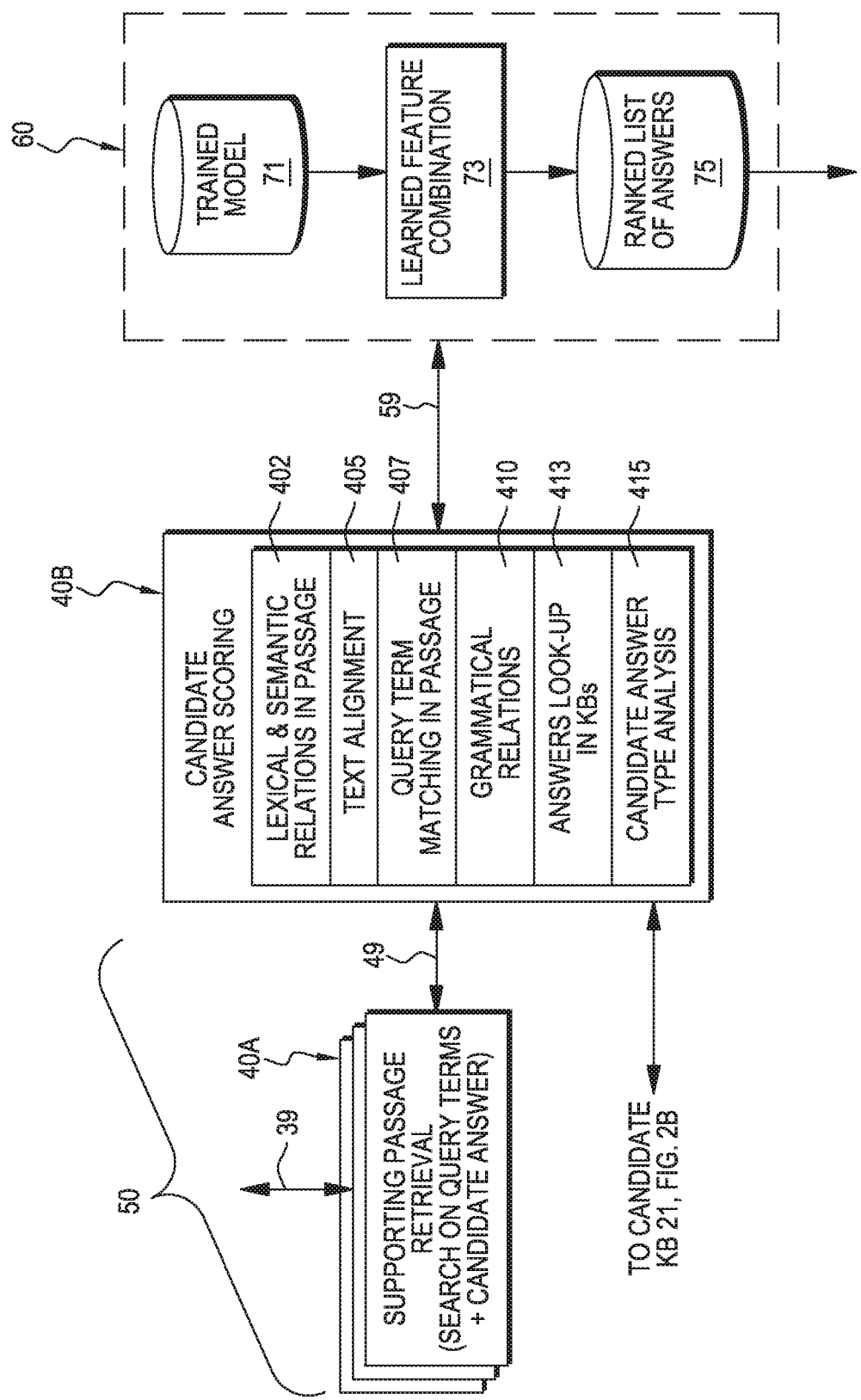
FIG. 4 shows a more detailed diagram of the Candidate Answer Scoring and the Answer Ranking Modules of FIGS. 1 and 2.

With reference to FIGS. 2 and 4, the "Candidate Answer Scoring" module 40B receives a CAS-type data structure 49 (i.e., CAS or CASes) output from the Supporting Passage Retrieval (SPR) block 40A of Evidence Gathering block 50, for example. The "Candidate Answer Scoring" module 40B includes, but is not limited to, one or more the following functional sub-processing modules: a Lexical & Semantic Relations in Passage module 402; a Text Alignment module 405; a Query Term Matching in Passage module 407; a Grammatical Relations block 410; an Answer Look-up in KBs module 413; and a Candidate Answer Type Analysis module 415.

The Lexical and Semantic Relations in Passage module 402 implements functions computing how well semantic (predicate/argument) relations in the candidate answer passages are satisfied (part of answer scoring). The Text Alignment module 405 implements functions for aligning the query (or portions thereof) and the answer passage and computing the score describing the degree of alignment, e.g., when aligning answers in a quotation. The Query Term Matching in Passage module 407 implements functions for relating how well a passage in the query matches to terms in the candidate answer passages (part of answer scoring). The Grammatical Relations block 410 implements functions for detecting a grammatical relations among candidate answers which can be subsumed under the Lexical & Semantic Relations in Passage module 402. The Answer Look-up in KBs module 413 implements functions for detecting the candidate answer based on the score ranking. The Candidate Answer Type Analysis module 415 produces a probability measure that a Candidate Answer is of the correct type based, e.g., on a grammatical and semantic analysis of the document with which the Candidate Answer appears. The output of the "Candidate Answer Scoring" module 40B is a CAS structure having a list of answers with their scores given by the modules.

As described herein, multiple parallel operating modules may be implemented to compute the scores of the candidate answers with the scores provided in CAS-type data structures 59 based on the above criteria. For instance, does the answer satisfy similar lexical and semantic relations (e.g. for a query about an actress starring in a movie, is the answer a female, and does the candidate satisfy actor-in-movie relation?), how well do the answer and the query align; how well do the terms match and do the terms exist in similar order. Thus, it is understood that multiple modules are used to process different candidate answers and, thus, potentially provide many scores in accordance with the number of potential scoring modules.

With reference to FIGS. 2 and 4, the "Answer Ranking" module 60 thus receives a plurality of CAS-type data structures 59 output from the Evidence Gathering block 50 (which includes implementing SPR 40A and Candidate Answer Scoring 40B), and generates a score for each candidate answer. FIG. 4 shows a machine learning implementation where the "Answer Ranking" module 60 includes a trained model component 71 produced using a machine learning techniques from prior data. The prior data may encode information on features of candidate answers, the features of passages the candidate answers come in, the scores given to the candidate answers by Candidate Answer Scoring modules 40B, and whether the candidate answer was correct or not. The machine learning algorithms can be applied to the entire content of the CASes together with the information about correctness of the candidate answer. Such prior data is readily available for instance in technical services support functions, or in more general settings on the Internet, where many websites list questions with correct answers. The model encodes a prediction function which is its input to the "Learned Feature Combination" module 73.

Thus, in the embodiment illustrated in FIG. 4, there is input to the answer ranking module 60 a list of candidate answers, as a CAS, in addition to a trained model that is stored in the trained model sub-module 71 and whose parameters depend on the type of the query. The answer ranking module 60 includes a learned feature combination sub-block 73 which implements functionality that generates a ranked list of answers 75. An output of the answer ranking module 60 includes an answer to the query (one or a list) and, optionally, a clarification question (if the system is engaging in a dialog or if none of the produced answers has a high rank). The learned feature combination sub-block 73 applies the prediction function produced by the Trained Model 71, and for example it implements methods that weight the scores of candidate answers based on the trained model. An example implementation of the training block 71 and of Learned Feature Combination 73 may be found in the reference to Ittycheriah, A. et al, entitled "{IBM}'s Statistical Question Answering System—{TREC}-"Text {REtrieval} Conference" in 2001 at ttp://citeseer.ist.ps-u.edu/cache/papers/cs2/7/http:
zSzzSztrec.nist.govzSzpubszSztrec10zSz.zSzpa perszSztrec2001.pdf/ittycheriah01ibms.pdf). The application of a machine learning Trained Model 71 and the Learned Feature Combination 73 are described below in more detail. In one embodiment, a two-part task is implemented to: (1) identify a best answer among candidates, and (2) determine a confidence in that best answer. In accordance with this processing, each question-candidate pair comprises an instance, and scores are obtained from a wide range of features, e.g., co-occurrence of answer and query terms, whether a candidate matches answer type, and search engine rank. Thus, for an example question, What at liquid remains after sugar crystals are removed from concentrated cane juice.?, example scores such as shown in the Table 1 below are generated based on but not limited to: Type Analysis, Alignment, Search Engine Rank, etc. TypeAgreement is the score for whether the lexical form of the candidate answer in the passage corresponds to the lexical type of the entity of interest in the question. Textual Alignment scores the alignment between question and answer passage.

TABLE 1

| Candidate | Type | Align | Rank | Score |
|---|---|---|---|---|
| Milk | 1 | 0.2 | 3 | 0.46 |
| Muscovado | 0 | 0.6 | 1 | 0.48 |
| Molasses | 1 | 0.5 | 2 | 0.8 |

Thus, in this embodiment, candidate answers are represented as instances according to their answer scores. As explained above, a classification model 71 is trained over instances (based on prior data) with each candidate answer being classified as true/false for the question (using logistic regression or linear regression function or other types of prediction functions as known in the art). This model is now applied, and candidate answers are ranked according to classification score with the classification score used as a measure of answer confidence, that is, possible candidate answers are compared and evaluated by applying the prediction function to the complete feature set or subset thereof. If the classification score is higher than a threshold, this answer is deemed as an acceptable answer. Using the numbers for Type, Align and Rank of Table I, and the prediction function (Score) given by an example linear expression: $=0.5*Type+0.8*Align+(1-Rank)*0.1$, values of 0.46, 0.48 and 0.8 are obtained for Milk, Muscovado and Molasses, respectively (the higher value being better. These values are represented in the Score column of TABLE 1. This example of the scoring function is given for illustration only, and in the actual application, more complex scoring functions may be used. For instance, the mathematical expression may be based on the logistic regression function (a composition of linear expressions with the exponential function), and may be applied to a much larger number of features.

Figure 5:
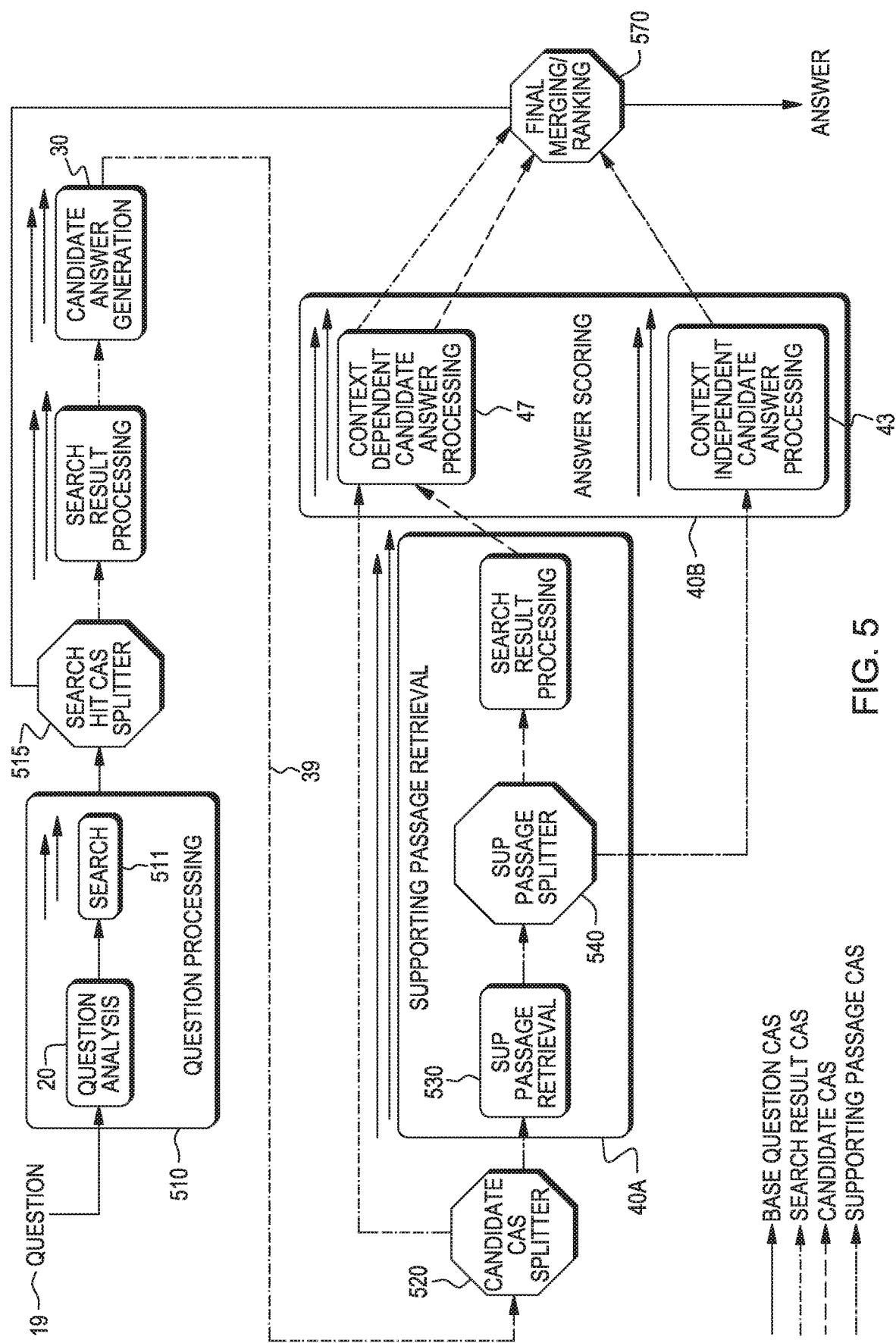
FIG. 5 is an example flow diagram depicting method steps for processing questions and providing answers according to an embodiment of the invention.

FIG. 5 is a block diagram 500 depicting system operation. At step 510, a query is received by the system programmed to perform the steps of the invention. The set of instructions are executed in a computing environment comprising one or more processors or computing devices. The query is analyzed and parsed into elements suitable for searching by the search engine 511 (performing the information retrieval function of module 30 in FIGS. 1 and 2).

FIG. 5 also represents a Data Model defining the data structures supplied as input to, or produced as output by, the system components shown in FIGS. 1 and 2. The Data Model provides documentation about what a given component does, and it enables independently developed components to be integrated with a fairly high degree of confidence that they will correctly inter-operate. The Data Model is formally defined as a UIMA Type System and has a declarative specification in a UIMA Type System descriptor. As known, the Unstructured Information Management Architecture (UIMA) framework is an open, industrial-strength, scalable and extensible platform for building analytic applications or search solutions that process text or other unstructured information to find the latent meaning, relationships and relevant facts buried within (http:// incubator.apache.org/uima/).

The Data Model is instantiated with a UIMA CAS (the container for instances of types in the type system.

The type system has a few basic design points.
1. A CAS represents a single question however, it is not so limited, i.e., includes the question of some prior focus (category, prior question or answer, or question meta-data some element of the context is also provided);
2. The question is the subject of analysis in the initial CAS view;
3. Processing is divided into several phases, where each phase may generate multiple, new CASes with new subjects of analysis and corresponding views, but the original question view is carried in every CAS. It is understood that variations are possible.

All processing results may be added to the original CAS (with intermediate results carrying the way through to the end of processing) and the final answer generated by the system is posted as an annotation in the CAS.

In one example embodiment, the data model includes a base annotation type that many of the types extend the uima.tcas.Annotation (see http://incubator.apache.org/UIMA). Each class (e.g., an annotator) can also provide an estimate of the correctness of the annotations it creates.

In one exemplary embodiment, as part of the question analysis performed during the questions processing phase 510, the question 19 is received and the CAS is initialized with the question (and the question context). Two initial annotations are created: a Question annotation with meta-data about the question, and a QaResult annotation that consolidates all of the question analysis results by either containing the results directly, or pointing to other annotations that represent question analysis results.

The base Question annotation type is defined to optionally include any associated meta-data such as the source of the question (TREC, technical support, TV show, etc.), prior dialog, or other contextual information (for example, about information contained in the input expressed in other modalities).

The question type can be further specialized into example subtypes modeling questions that Question which class defines a Type (i.e., question type, for example, one of FACTOID, LIST, DEFINITION, OTHER, OPINION or UNCLASSIFIED question types).

An initial step in analyzing the question is to run the NLP (Natural Language Processing) stack on the question. Natural language processing typically includes syntactic processing (e.g. using the ESG parser) and derivation of predicate-argument structure. This processing is performed in accordance with the standard UIMA fashion, where the NLP stack is run as an aggregate analysis engine on the CAS. In an embodiment of the invention, all of the NLP stack results are added to the CAS as annotations extending Hutt and ESG type systems.

After NLP stack processing, the question analysis components are run, which include question classification, answer type detection, and focus identification, for example, as shown in the query analysis block of FIG. 3. The question may be classified based on question types (metadata), each of which may require special downstream processing. The result of this classification may be stored in a QClass annotation:

Example downstream processing may include processing a puzzle question (where getting the answer requires synthesis information from multiple sources, inference, etc.); an audio visual question that requires audio/visual processing; a simple_factoid question with quotes, or named entities, etc.; a FACTOID about a fact that can be "looked up"; and a DEFINITION that contains a definition of the answer and where the words defined by the question are expected as an answer.

The typical question analysis processes shown in FIG. 3 produces several annotations, including the focus, answer type, semantic role labels, and constraints, and marks any portion of the question that represents a definition.

For the above annotation types, the Question Analysis component 510 of FIG. 5 will create an instance of the annotation, set the span over the question text (if appropriate), and set any other features in the annotation. Note that there may be multiple instances of these annotations.

The question and the results of question analysis are used to generate an abstract representation of the query, which for purposes of description, is referred to as the AbstractQuery. The abstract query represents all searchable keywords and phrases in the question, along with the semantic answer type (if it was detected).

The abstract query is represented using the following types: a synonym (all query concepts underneath are synonyms of each other); a phrase (all query concepts in order are a phrase); a tie (an "or", i.e., a disjunction of the argument nodes); a weight (the concepts underneath are weighted per the float stored in the operator); required (the concepts underneath are all required, if possible); and relation (the concepts underneath are below a relation, which is stored within the operator).

Referring to FIG. 5, in question processing block 510, after question analysis and possible decomposition, search processing begins, and this may include searching primary structured and unstructured sources, e.g. Google, a local copy of Wikipedia, or database look-up.

Each search engine has a query generator that generates an engine-specific query from the abstract query and formats it in the query syntax for the search engine. The search engine then processes the query and adds a search result hit-list to the CAS. A Search object contains the search engine query, an identifier for the search engine, and the search results.

In one embodiment, a search result is represented by a SearchResult object, which contains an identifier for the result (a URI), a score for the result, and the actual content of the result, i.e., the passage text, knowledge base tuple, etc. The SearchResult may be specialized for different kinds of search engines and corresponding search results.

The Document object may be created to represent the result delivered by the search engine. This object may include a title of the document and a unique identifier for this document, and other data and meta-data. The passage object may be used with a search engine that returns passages. It may add to the document object the offset (e.g., a character offset of the start of this passage within the document that contains this passage, and a character offset of the end of this passage within the document that contains this passage) and passage length metadata for the passage hit.

As represented in FIG. 5, the data in the example CAS structure are output of the search results block of the question analysis processing step 510 and are about to be processed in parallel. A Search Hit CAS splitter mechanism 515 is used to initiate a parallel search for candidate answers. For parallel operations, the search list (search result passages) are distributed by the CAS splitter element 515 so that concurrent search results processing techniques are applied (work divided) to process each of the found search results and to perform candidate answer generation (in parallel) using the techniques described herein in the Candidate Answer Generation block 30 (FIG. 3).

During candidate answer generation, candidate answers are identified in the search result. In one example implementation, a candidate answer is represented at two different levels: a Candidate Answer Variant; and A Candidate Answers Canon. A CandidateAnswerVariant is a unique candidate answer string (possibly the result of some very simple normalization). A CandidateAnswerCanon is a canonicalized candidate answer that groups together semantically equivalent variants. Both of these types extend an abstract base class CandidateAnswer which class defines the candidate answer string and features associated with this candidate answer.

A class (e.g., CandidateAnswer) for candidate answers provides the candidate answer string and features associated with this candidate answer. In operation, one or more of its subtypes may be instantiated. One sub-type includes a variant of a candidate answer class (CandidateAnswerVariant) defined that may have multiple occurrences, all of which are collected in a variant object and defines the occurrences of this variant. A CandidateAnswerOccurrence class is provided that annotates a span of text identified as a candidate answer and defines: (1) the manner in which covered text refers to some entity, e.g. NAME, PRONOUN, CITY; (2) the source of the candidate answer; (3) the character offset of the start of this candidate answer within the text of the source; and (4) the character offset of the end of this candidate answer within the text of the source.

In one example implementation, candidate answers are derived from document titles, and another method may derive a candidate answer from one or more elements in the candidate passage. Candidate answers can be normalized whereby several spelling variants can be identified in one canonical form.

The data in the example CAS structure 39 output of the search results processing and candidate answer generation block 30 is again processed in parallel by a Candidate Answer CAS splitter mechanism 520 that is used to parallelize the candidate answers for input to the Supporting Passage Retrieval block 40A. For each set of candidate answers, the CAS is split into separate CASes such that each CAS includes one or more candidate answers and is sent to evidence gathering module 50 for processing.

The Evidence Gathering module 50 (shown in FIGS. 1 and 3) that implements (parallel processing) and supports passage retrieval and answer scoring according to embodiments of the invention is now described in greater detail with respect to FIG. 5.

Traditionally, passage retrieval is used in candidate answer generation wherein using keywords from the question, passages are found from unstructured corpora. Then candidate answers are extracted from those passages.

In accordance with an embodiment of the present invention, Supporting Passage Retrieval (SPR) operates after candidate answer generation. For each resulting candidate passage, the passage content are traversed to find/look for those passages having candidate answers in addition to question terms. It is understood that better passages can be found if it is known what candidate answer is being looked for. For each resulting candidate, the sources are traversed to find those passages having candidate answers in addition to question terms (i.e., another search is conducted against the original primary sources (databases) or the Candidate KB). In another embodiment, the search can be conducted against cached search results (past passages). It is understood that the best results are obtained if the search is repeated with candidate answers included together with the question terms.

As mentioned above, current information retrieval and question answering systems attempt to satisfy a user's information need by identifying the single document segment (e.g., entire document, contiguous sequence of one or more sentences, or a single phrase) that is most likely to contain relevant information. There are many information needs that cannot be satisfied by a single document segment.

Rather, the information retrieval system must identify a number of relevant document segments and further analyze or synthesize the information contained in those segments to satisfy the user's information need.

Embodiments of the invention address this challenge by using logical proofs to guide the search. A final conclusion that is produced in response to a query may be only indirectly derived from content found in multiple documents. For example, a question such as "Who was Henry VI's paternal grandfather?" might be answered by separate documents that state that "Henry VI's father was Henry V" and that "Henry V's father was Henry IV." Once a system has derived a conclusion (e.g., "Henry IV is Henry VI's paternal grandfather"), it may be expected to provide support for that conclusion by citing original sources.

There may be multiple distinct proofs that can be found for any given conclusion. Each of these proofs will involve some set of premises, i.e., facts that are directly asserted in source material. Any given premise may be mentioned in one or more source documents. Any set of documents that contains mentions of all of the premises for some proof of a conclusion can be said to provide adequate support for that conclusion. Smaller sets of documents are generally preferable to larger sets since they typically involve less effort from a user to confirm that a conclusion is valid. Embodiments of the invention include a mechanism for identifying minimal or quasi-minimal sets of documents that provide adequate support for a conclusion derived through logical deduction.

Embodiments of the mechanism and procedure for identifying these minimal or quasi-minimal sets of documents include two phases: indexing and retrieval. For example, one procedure for indexing is illustrated in FIG. 6, and a procedure for retrieving documents is illustrated in FIG. 7.

Figure 6:
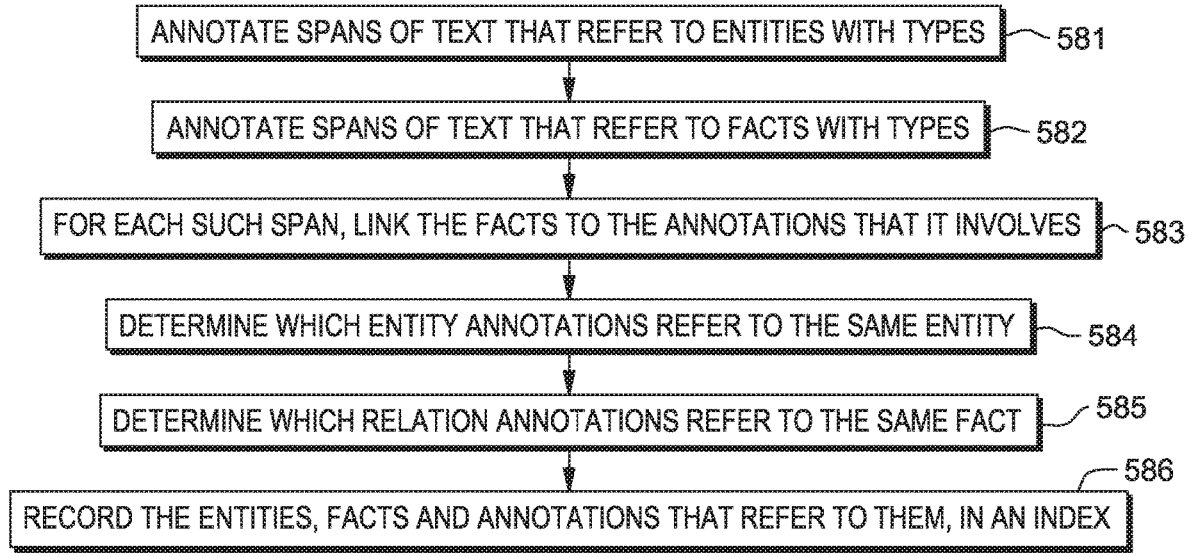
FIG. 6 illustrates a procedure for indexing documents in accordance with an embodiment of the invention.

With reference to FIG. 6, given a set of documents, a series of steps are taken for each document. Step 581 is to annotate spans of text that refer to entities with types, and step 582 is to annotate spans of text that refer to facts with types. For each such span, these facts are linked, at step 583, to the annotations that the span involves. Step 584 is to determine which entity annotations refer to the same entity, and step 585 is to determine which relation annotations refer to the same fact. Step 586 is to record the entities, facts and the annotations that refer to these entities and facts, in an index.

Figure 7:
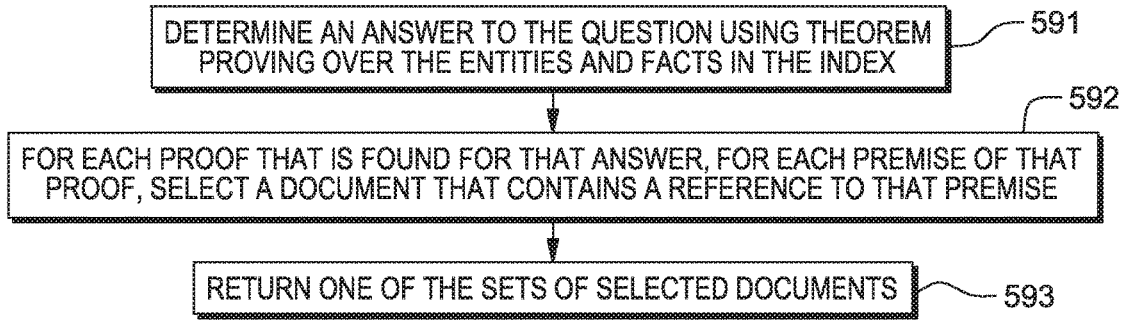
FIG. 7 shows a procedure for answering a question and identifying a set of supporting documents in accordance with an embodiment of the invention.

FIG. 7 shows a method for answering a question and providing supporting documents. In this method, given a question and an index, for example as constructed above, step 591 is to determine an answer to the question using theorem proving over the entities and facts in the index. At step 592, for each proof that is found for that answer, for each premise of that proof, a document is selected that contains a reference to that premise. Step 593 is to return one of the set of the selected documents.

One aspect in the above method is the selection of documents. Determining a minimal set for a given proof may under some circumstances be intractable for proofs that contain many premises that are mentioned in many documents. However, a method in which documents are added in decreasing order of the number of premises that they cover is likely to produce quasi-minimal sets of documents and can be proven to run with acceptable worst-case performance.

For example, consider the question: "Doe Bob own an ignition coil?". One proof of an answer to this question is comprised of the following seven premises (A-G):
A: Bob owns a Ford Taurus
B: A Ford Taurus is a sedan
C: A sedan is a car
D: A car is a motor vehicle
E: An engine is a part of a motor vehicle
F: A spark plug is a part of an engine
G: An ignition coil is part of a spark plug.

In this example, six documents (1-6) are found that contain some subsets of these premises, as shown in the following table.

| a. | Document | Premises found |
| b. | Number | in the document |
|---|---|---|
| | 1) | A |
| | 2) | A, B, C, D, E |
| | 3) | B |
| | 4) | F, G |
| | 5) | B, C, D, F |
| | 6) | B, C, G |

The true minimal set of documents that cover all the premises is comprised of documents 2 and 4. The greedy algorithm would start with document (2) (because it has the most premises). Next, the algorithm would add to this set document number (5) (which has the next most premises), and then add document number 6 (again, because this has the next most premises). At that point all of the premises would be covered by at least one document in the formed set so the algorithm would stop. Since the algorithm never got to document (4), this algorithm never noticed that documents (2) and (4) alone would answer the question. The main advantage of this greedy algorithm is that the algorithm never had to consider documents like documents (1) and (3) that do not add any extra value.

A variation of this greedy algorithm takes into consideration which premises have already been covered by documents already selected for inclusion, and at each iteration, selects the document that covers the most number of premises that have not been matched. It is slightly more expansive at runtime, but may yield better results than the previous algorithm. In this example, the same document (2) is selected at the first step, after which the system realizes that only premises F and G are unmatched. Next it selects document (4), which matches both premises and adds it to the set. This alternative algorithm produces the true minimal set containing documents (2) and (4) in this example.

After supporting documents, or supporting document sets, are found for a candidate answer, Supporting Passages are then scored by multiple Scorers by conducting one or more of the following: Simple Term Match Score; textual Alignment; and a deeper analysis. Simple Term Match Score implements executable instructions for counting the number of terms that match, and Textual Alignment implements executable instructions for determining if words appear in the same or similar order with a similar distance between them so they are not separated much (aligned). This is advantageous to find a quotation. To find quotes, for example, an alignment would be performed to get the best result. Deeper analysis implements executable instructions for determining the meaning of the passages/question (i.e., lexical and/or semantic relations). Each of these analyses produces a score.

An example Evidence Gathering is now described for non-limiting, illustrative purposes. In this example, a query is given as follows:

'In 2002, who became the first Republican sitting senator ever to host Saturday Night Live?'

In the Query Generation implementing stopword removal (that is removal from the query of the most frequent words such as "a", "an", "the", "is/was/be . . . ", "become/became . . . " . . . ), the query becomes: 'Republican first sitting senator ever host Saturday Night Live 2002'.

After query generation, in one embodiment, the query is sent to an Internet search engine, e.g., such as provided by MSN, and the top 20 result documents are read. The following depicts example passage extraction results (candidate answers) for the example question search results for 'Republican first sitting senator ever host Saturday Night Live 2002'. In each document, passages are identified that include each candidate answer (i.e., John McCain or Al Gore), along with as many question keywords as possible shown italicized. Both example passages include a passage score that, in one exemplary embodiment, is calculated as:

Passage Score= # of query terms in passage/total # of query terms

Candidate: John McCain
Document: http://doney.net/aroundaz/celebrity/mccain_john.htm Passage: Representative from Arizona 1st District (1983-1987), POW (1967-1972), Navy pilot, first sitting Senator to host Saturday Night Live (2002) Born in the Panama Canal Zone, John McCain shares the headstrong, blunt, maverick traits of his father and grandfather, who were the first father and son four star Admirals in the U.S.
Passage Score: 8/11=0.73
Candidate: Al Gore
Document: http://www.imdb.com/title/tt0072562/news Passage: 17 Dec. 2002 (StudioBriefing) No longer a candidate for the presidency in 2004, Al Gore may have a whole new career cut out for him as the host of a late-night comedy show, judging by the ratings for the December 14 edition of NBC's Saturday Night Live.
Passage Score: 5/11=0.45

Additionally calculated, in one embodiment, is an SPR Answer Score that is calculated, in one embodiment, as a decaying sum of scores of passages containing that answer as shown in equation 1)

$$\text{AnswerScore} = P_0 + nP_1 + n^2P_2 + n^3P_3 + \ldots \quad 1)$$

where, $P_i$ is the $i^{th}$ highest passage score, and "n" is a constant <1 (e.g., 0.1).

Thus, for the example query 'Republican first sitting senator ever host "Saturday Night Live" 2002," the SPR "AnswerScore" for Candidate John McCain is calculated as:

1) Taking the first candidate answer passage for John McCain with question keywords shown italicized, to wit:

Representative from Arizona 1st District (1983-1987), POW (1967-1972), Navy pilot, first sitting Senator to host Saturday Night Live (2002). Born in the Panama Canal Zone, John McCain shares the headstrong, blunt, maverick traits of his father and grandfather, who were the first father and son four star Admirals in the U.S. there is calculated a passage score of [Score: 0.74].

b. 2) Taking an example second candidate answer passage for John McCain, to wit:
John McCain, Meghan regaled reporters with tales of her days as an intern at Saturday Night Live in 2004. " Slave work, " she says, " but I had an amazing time. There is calculated a passage score of [Score: 0.27].

c. 3) Taking an example third candidate answer passage for John McCain, to wit:
The most prominent Republican Arizona Senator John McCain was portrayed as a loser because of his support for staying the course in Iraq. There is calculated a passage score of [Score: 0.18].

Thus, a Combined AnswerScore for candidate answer John McCain, in accordance with equation 1), with n=0.1, becomes: 0.74+(0.1)(0.27)+(0.01)(0.18)=0.7688.

Similarly, for the example query "2002 Republican first sitting senator ever host Saturday Night Live," the SPR "AnswerScore" for Candidate Al Gore is calculated as:

1) Taking the first candidate answer passage for Al Gore with question keywords shown italicized, to wit:

17 Dec. 2002 (StudioBriefing) No longer a candidate for the presidency in 2004, Al Gore may have a whole new career cut out for him as the host of a late-night comedy show, judging by the ratings for the December 14 edition of NBC's Saturday Night Live30, there is calculated a passage score of [Score: 0.45].

b. 2) Taking the second candidate answer passage for Al Gore, to wit:
Also in attendance were former Presidents George Bush, Gerald Ford, Jimmy Carter, former Vice-president Al Gore former Senator Bob Dole and all their wives. Was portrayed on "Saturday Night Live" (1975) by Phil Hartman, Chris Farley (once), David Spade (once), Chris Elliot (once), Michael McKean, and Darrell Hammond. There is calculated a passage score of [Score: 0.36].

c. 3) Taking the third candidate answer passage for Al Gore, to wit:
Also in attendance were former Presidents George Bush, Gerald Ford, Jimmy Carter, former Vice President Al Gore, former Senator Bob Dole and all their wives. [September 2001]. Was portrayed on "Saturday Night Live" (1975) by Phil Hartman, Chris Farley (once), David Spade (once), Chris Elliott (once), Michael McKean, and Darrell Hammond. There is calculated a passage score of [Score: 0.36].

d. 4) Taking the fourth candidate answer passage for Al Gore, to wit:
Remember Al Gore's "Saturday Night Live" skit where he pretended to be President and the world was a glorious place? There is calculated a passage score of [Score: 0.27].

Thus, a Combined AnswerScore for candidate answer Al Gore, as calculated by the SPR module in accordance with equation 1), becomes: 0.45+(0.1)(0.36)+(0.01)(0.36)=0.4896.

It is noted that an Answer scoring in accordance with a simple sum scheme would have been 1.44 for Al Gore, which would have beat a score of 1.19 in a simple sum calculation for John McCain.

The answer scores for each candidate answer would be included in the CAS.

Referring back to FIG. 5, in module 530, supporting passages are retrieved. Functionality is initiated after the CAS split. Supporting passage records created by Supporting Passage Retrieval are split by Supporting Passage Splitter 540; and since there may be many of them, the splitter routes the new CASes (with all information that was computed previously: context, query, candidate answer, supporting passage) to Answer Scoring.

The results contain many CASes containing (among other elements) the three important items: a candidate answer, the question terms, and a supporting passage. Since thousands of such CASes can be generated per one question, these candidates are scored in parallel. In an embodiment, the candidate scoring performed by candidate scoring module 40B can be subdivided into two classes: context independent scoring 43 (where the answer can be scored independently of the passage), and context dependent scoring 47 (where the answer score depends on the passage content). For example, if the candidate answer is obtained from the document title, the score will not be dependent on the content of the passage, and are context independent. In constrast, other types of candidate answer scoring based on text alignment (module 405, FIG. 4), grammatical relations (module 410, FIG. 4), or lexical and semantic relations (module 402, FIG. 4) require a comparison between the query and the passage, and are context dependent. Since most of these methods depend on the computation of grammatical and semantic relations in the passage, search results must be processed (in the Search Result Processing module in SPR block 40A) prior to Context Dependent Candidate Answer processing in 47.

The results of an answer scorer are saved in the CAS. During the final phase of Answer Ranking processing 60, all of the candidate answer features are aggregated and merged, and the final candidate answer scoring function is applied (as described above with respect to the example scores provided in Table 1. Since a given candidate answer may appear in multiple passages, the Final Merge/Rank annotator must collect results across CASes, normalize and merge candidate answers, merge feature scores produced by the same answer scorer across multiple instances of the candidate answer, and aggregate the results. The normalized, merged, and aggregated results are input to the scoring function to produce a final score for the candidate answer. The final scoring results are saved as an answer and/or delivered to a user. In embodiments of the invention, Final merging and ranking is incremental, i.e., the machine provides the best answer so far as the computation on different nodes completes. Once all nodes complete, the final (top) answer(s) is delivered. Thus, in one embodiment, the final AnswerList and Answers are added to the original Question view, and the question answering process is complete.

It should also be noted that if the system is unable to find an answer or to find an answer with a high score (based, e.g., upon comparison to a preset threshold), the system might ask the user a clarifying question, or deliver a collection of answers, or admit a failure and ask the user for further direction. A person skilled in the art would be able to implement such a dialog based e.g. on U.S. Pat. Nos. 6,829,603 and 6,983,252, both of which are incorporated by reference as if fully set forth herein, and a reference entitled "Natural language dialogue for personalized interaction" authored by Wlodek Zadrozny, et al. and found in Communications of the ACM archive, Volume 43, Issue 8, (August 2000), Pages: 116-120, (http://portal.acm.org/citation.cfm?id=345164).

A person skilled in the art would be able to implement a further extension to the system of the invention to employ modes of multimodal communication (using U.S. Pat. No. 7,136,909) involving multiple modalities of text, audio, video, gesture, tactile input and output etc. As mentioned above, examples of such interaction include a cell phone user who is asking a question using voice and is receiving an answer in a combination of other modalities (voice, text and image), or an interaction with a video game.

The data model and processing models described herein are designed to enable parallel processing, and to admit a "streaming" model of computation, where results become available incrementally, before all processing is complete. This streaming model may be advantagoues if the analytics are able to identify and process the most likely candidates first, and continue to improve scoring estimates with more processing time.

As mentioned, in one embodiment, the above-described modules of FIGS. 1-7 can be represented as functional components in UIMA and may be embodied as a combination of hardware and software for developing applications that integrate search and analytics over a combination of structured and unstructured information. The software program that employs UIMA components to implement end-user capability is generally referred to as the application, the application program, or the software application.

The UIMA high-level architecture, one embodiment of which is illustrated in FIGS. 1-7, defines the roles, interfaces and communications of large-grained components that cooperate to implement UIM applications. These include components capable of analyzing unstructured source artifacts, such as documents containing textual data and/or image data, integrating and accessing structured sources and storing, indexing and searching for artifacts based on discovered semantic content.

Although not shown, a non-limiting embodiment of the UIMA high-level architecture includes a Semantic Search Engine, a Document Store, at least one Text Analysis Engine (TAE), at least one Structured Knowledge Source Adapter, a Collection Processing Manager, at least one Collection Analysis Engine, all interfacing with application logic. In one example embodiment, the UIMA operates to access both structured information and unstructured information to generate candidate answers and an answer in the manner as discussed herein. The unstructured information may be considered to be a collection of documents, and can be in the form of text, graphics, static and dynamic images, audio and various combinations thereof.

Figure 8:
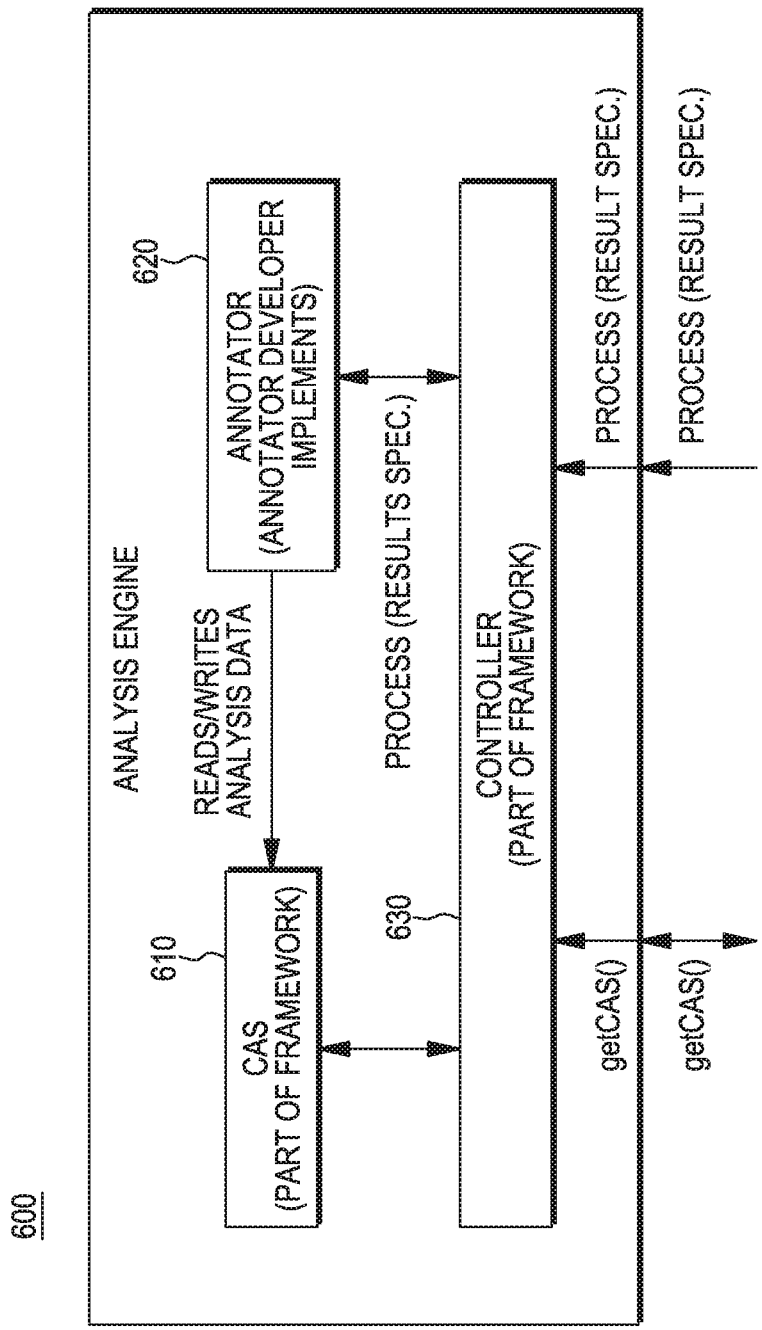
FIG. 8 depicts an aspect of a UIMA framework implementation for providing one type of analysis engine for processing CAS data structures.

Aspects of the UIMA are further shown in FIG. 8, where there is illustrated an Analysis Engine (AE) 600 that can be a component part of the Text Analysis Engine. Included in the AE 600 is a Common Analysis System (CAS) 610, an annotator 620 and a controller 630. A second embodiment of a TAE (not shown) includes an aggregate Analysis Engine composed of two or more component analysis engines as well as the CAS, and implements the same external interface as the AE 600.

Common Analysis System 610

The Common Analysis System (CAS) 610 is provided as the common facility that all Annotators 620 use for accessing and modifying analysis structures. Thus, the CAS 610 enables coordination between annotators 620 and facilitates annotator 620 reuse within different applications and different types of architectures (e.g. loosely vs. tightly coupled). The CAS 610 can be considered to constrain operation of the various annotators.

The CAS 610 principally provides for data modeling, data creation and data retrieval functions. Data modeling preferably defines a tree hierarchy of types, as shown in the example Table 2 provided below. The types have attributes or properties referred to as features. In embodiments of the invention, there are a small number of built-in (predefined) types, such as integer (int), floating point (float) and string; UIMA also includes the predefined data type "Annotation". The data model is defined in the annotator descriptor, and shared with other annotators. In the Table 2, some 뵤ypes ? that are considered extended from prior art unstructured information management applications to accommodate question answering in embodiments of the invention include:

TABLE 2

| TYPE (or feature) | TYPE's PARENT (or feature type) |
|---|---|
| Query Record | Top |
| Query | Query Record |
| Query Context | Query Record |
| Candidate Answer Record | Annotation |
| Candidate Answer | Candidate Answer Record |
| Feature: CandidateAnswerScore | Float |
| Supporting Passage Record | Candidate Answer Record |
| Feature: SupportingPassageScore | Float |

In Table 2, for example, all of the question answering types (list in the left column) are new types and extend either another new type or an existing type (shown in the right column). For example, both Query and Query Context are kinds of Query Record, a new type; while Candidate Answer Record extends the UIMA type Annotation, but adds a new feature CandidateAnswerScore which is a Float.

CAS 610 data structures may be referred to as "feature structures." To create a feature structure, the type must be specified (see TABLE 2). Annotations (and—feature structures) are stored in indexes.

The CAS 610 may be considered to be a collection of methods (implemented as a class, for example, in Java or C++) that implements an expressive object-based data structure as an abstract data type. Preferably, the CAS 610 design is largely based on a TAE 130 Feature-Property Structure, that provides user-defined objects, properties and values for flexibility, a static type hierarchy for efficiency, and methods to access the stored data through the use of one or more iterators.

The abstract data model implemented through the CAS 610 provides the UIMA 100 with, among other features: platform independence (i.e., the type system is defined declaratively, independently of a programming language); performance advantages (e.g., when coupling annotators 620 written in different programming languages through a common data model); flow composition by input/output specifications for annotators 620 (that includes declarative specifications that allow type checking and error detection, as well as support for annotators (TAE) as services models); and support for third generation searching procedures through semantic indexing, search and retrieval (i.e. semantic types are declarative, not key-word based).

The CAS 610 provides the annotator 620 with a facility for efficiently building and searching an analysis structure. The analysis structure is a data structure that is mainly composed of meta-data descriptive of sub-sequences of the text of the original document. An exemplary type of meta-data in an analysis structure is the annotation. An annotation is an object, with its own properties, that is used to annotate a sequence of text. There are an arbitrary number of types of annotations. For example, annotations may label sequences of text in terms of their role in the document's structure (e.g., word, sentence, paragraph etc), or to describe them in terms of their grammatical role (e.g., noun, noun phrase, verb, adjective etc.). There is essentially no limit on the number of, or application of, annotations. Other examples include annotating segments of text to identify them as proper names, locations, military targets, times, events, equipment, conditions, temporal conditions, relations, biological relations, family relations or other items of significance or interest.

Typically an Annotator's 620 function is to analyze text, as well as an existing analysis structure, to discover new instances of the set of annotations that it is designed to recognize, and then to add these annotations to the analysis structure for input to further processing by other annotators 220.

In addition to the annotations, the CAS 610 of FIG. 6 may store the original document text, as well as related documents that may be produced by the annotators 620 (e.g., translations and/or summaries of the original document). Preferably, the CAS 610 includes extensions that facilitate the export of different aspects of the analysis structure (for example, a set of annotations) in an established format, such as XML.

More particularly, the CAS 610 is that portion of the TAE that defines and stores annotations of text. The CAS API is used both by the application and the annotators 620 to create and access annotations. The CAS API includes, for example, three distinct interfaces. A Type system controls creation of new types and provides information about the relationship between types (inheritance) and types and features. One non-limiting example of type definitions is provided in TABLE 1. A Structure Access Interface handles the creation of new structures and the accessing and setting of values. A Structure Query Interface deals with the retrieval of existing structures.

The Type system provides a classification of entities known to the system, similar to a class hierarchy in object-oriented programming. Types correspond to classes, and features correspond to member variables. Preferably, the Type system interface provides the following functionality: add a new type by providing a name for the new type and specifying the place in the hierarchy where it should be attached; add a new feature by providing a name for the new feature and giving the type that the feature should be attached to, as well as the value type; and query existing types and features, and the relations among them, such as "which type(s) inherit from this type".

In an embodiment, the Type system provides a small number of built-in types. As was mentioned above, the basic types are int, float and string. In a Java implementation, these correspond to the Java int, float and string types, respectively. Arrays of annotations and basic data types are also supported. The built-in types have special API support in the Structure Access Interface.

The Structure Access Interface permits the creation of new structures, as well as accessing and setting the values of existing structures. In an embodiment, this provides for creating a new structure of a given type, getting and setting the value of a feature on a given structure, and accessing methods for built-in types. Feature definitions are provided for domains, each feature having a range.

In an alternative environment, modules of FIGS. 1-7 can be represented as functional components in GATE (General Architecture for Text Engineering) (see: http://gate.ac.uk/releases/gate-2.0alpha2-build484/doc/userguide.html).

GATE employs components which are reusable software chunks with well-defined interfaces that are conceptually separate from GATE itself. All component sets are user-extensible and together are called CREOLE—a Collection of REusable Objects for Language Engineering. The GATE framework is a backplane into which plug CREOLE components. The user gives the system a list of URLs to search when it starts up, and components at those locations are loaded by the system. In one embodiment, only their configuration data is loaded to begin with; the actual classes are loaded when the user requests the instantiation of a resource). GATE components are one of three types of specialized Java Beans: 1) Resource; 2) Processing Resource; 3) Language Resource; and 4) Visual Resource.

Resource is a top-level interface, which describes all components. What all components share in common is that they can be loaded at runtime, and that the set of components is extendable by clients. They have Features, which are represented externally to the system as "meta-data" in a format such as RDF, plain XML, or Java properties. Resources may all be Java beans in one embodiment. ProcessingResource is a resource that is runnable, may be invoked remotely (via RMI), and lives in class files. In order to load a PR (Processing Resource), the system knows where to find the class or jar files (which will also include the metadata). Language Resource is a resource that consists of data, accessed via a Java abstraction layer. They live in relational databases. VisualResource is a visual Java bean, component of GUIs, including of the main GATE gui. Like PRs these components live in .class or .jar files.

In describing the GATE processing model, any resource whose primary characteristics are algorithmic, such as parsers, generators and so on, is modelled as a Processing Resource. A PR is a Resource that implements the Java Runnable interface. The GATE Visualisation Model implements resources whose task is to display and edit other resources are modelled as Visual Resources. The Corpus Model in GATE is a Java Set whose members are documents. Both Corpora and Documents are types of Language Resources (LR) with all LRs having a Feature Map (a Java Map) associated with them that stores attribute/value information about the resource. FeatureMaps are also used to associate arbitrary information with ranges of documents (e.g. pieces of text) via an annotation model. Documents have a DocumentContent which is a text at present (future versions may add support for audiovisual content) and one or more AnnotationSets which are Java Sets.

As UIMA, GATE can be used as a basis for implementing natural language dialog systems and multimodal dialog systems having the disclosed question answering system as one of the main submodules. The references, incorporated herein by reference above (U.S. Pat. Nos. 6,829,603 and 6,983,252, and 7,136,909) enable one skilled in the art to build such an implementation.

Embodiments of the invention can take the form of an entirely hardware embodiment, an entirely software embodiment or an embodiment containing both hardware and software elements. In embodiments, the invention is implemented in software, which includes but is not limited to firmware, resident software, microcode, etc.

The invention can take the form of a computer program product accessible from a computer-usable or computer-readable medium providing program code for use by or in connection with a computer or any instruction execution system. For the purposes of this description, a computer usable or computer readable medium can be any apparatus that can contain, store, communicate, propagate, or transport the program for use by or in connection with the instruction execution system, apparatus or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read only memory (ROM), a rigid magnetic disk and an optical disk. Current examples of optical disks include compact disk read only memory (CD-ROM), compact disk read/write (CD-R/W), and DVD.

The system and method of the present disclosure may be implemented and run on a general-purpose computer or computer system. The computer system may be any type of known or will be known systems and may typically include a processor, memory device, a storage device, input/output devices, internal buses, and/or a communications interface for communicating with other computer systems in conjunction with communication hardware and software, etc.

The terms "computer system" and "computer network" as may be used in the present application may include a variety of combinations of fixed and/or portable computer hardware, software, peripherals, and storage devices. The computer system may include a plurality of individual components that are networked or otherwise linked to perform collaboratively, or may include one or more stand-alone components. The hardware and software components of the computer system of the present application may include and may be included within fixed and portable devices such as desktop, laptop, and server. A module may be a component of a device, software, program, or system that implements some "functionality", which can be embodied as software, hardware, firmware, electronic circuitry, or etc.

In the preferred embodiment the term "user" refers to a person or persons interacting with the system, and the term "user query" refers to a query posed by the user. However other embodiments can be constructed, where the term "user" refers to the computer system generating a query by mechanical means, and where the term "user query" refers to such a mechanically generated query. In this context the "user query" can be a natural language expression, a formal language expression, or a combination of natural language and formal language expressions. The need for automated answering of a computer generated questions arises, for example, in the context of diagnosing failures of mechanical and electronic equipment, where the failing equipment can generate a query on the best way to fix a problem, and such a query could be answered by the system described in this invention based on a relevant corpus of textual data collected from the Internet. Methods of generating automatically natural language expressions from a formal representation have been previously disclosed, for example, in the U.S. Pat. Nos. 5,237,502 and 6,947,885, the contents and disclosures of each of which are incorporated by reference as if fully set forth herein and, can be used by the skilled in the art to create systems for automatically issuing a "user query". Similarly, in such a diagnostic scenario the system can ask an elaboration question, e.g. to query for some additional parameters.

The embodiments described above are illustrative examples and it should not be construed that the present invention is limited to these particular embodiments. Thus, various changes and modifications may be effected by one skilled in the art without departing from the spirit or scope of the invention as defined in the appended claims.

The invention claimed is:

1. A computer-implemented method of searching through a database of documents for documents to generate a score for a candidate answer to an input query, the method comprising:
 indexing, by a computer processor system, the documents in the database, including
  for each of the documents, annotating, by the computer processor system, spans of text in said each document that refer to entities with entity types to form entity annotations, and annotating, by the computer processor system, spans of text in said each document that refer to facts with fact types to form relation annotations, for each of the annotated spans of text that refers to one of the facts, linking, by the computer processor system, said one of the facts to said each annotation, and recording, by the computer processor system, in an index, the entities, the facts, the annotations that refer to said entities, and the annotations that refer to said facts;

receiving an input query at the computer processor system;

identifying, by the computer processor system, a candidate answer to the input query;

determining at the computer processor system a set of documents in the database using said index and theorem proving for scoring the candidate answer, including:

identifying, by the computer processor system, a logical proof of the candidate answer, the logical proof including a conclusion and a sequence of premises that logically prove the conclusion, including using the candidate answer as the conclusion of the logical proof;

searching, by the computer processor system, through a group of documents to identify a sub-group of documents of the group of documents, each document of the sub-group of documents including one or more of the premises of the logical proof, and wherein each of the premises of the logical proof is included in at least one of the documents of the sub-group of documents;

using, by the computer processor system, an iterative process, including a sequence of steps, to select, from said sub-group of documents, a set of documents that establish all the premises of the logical proof, including at each of the steps of the iterative process, selecting for said set of documents one of the documents that, of the documents of said sub-group of documents, has the largest number of the premises of the logical proof that, at the time of said each step, are not included in any of the documents in the set of documents; and using, by the computer processor system, the set of documents to generate a score for the candidate answer.

2. The method according to claim 1, wherein the indexing the documents in the database includes:
determining which of the entity annotations refer to the same fact; and
determining which of the relation annotations refer to the same fact.

3. The method of claim 1, wherein the using, by the computer processor system, an iterative process further includes recognizing after each of the steps the premises of the logical proof that are not in any of the documents in the set of documents.

4. The method according to claim 1, wherein the using the iterative process further includes selecting for said set of documents a first document of said sub-group of documents that, of the documents of said sub-group of documents, has the most of the premises of the logical proof.

5. The method according to claim 1, wherein the using the iterative process further includes continuing with the iterative process until each of the premises is included in at least one of the documents of said set of documents.

6. The method according to claim 1, wherein the searching through a group of documents to identify a sub-group of documents of the group of documents that include one or more of the premises includes identifying a number of the premises in said each document of said sub-group of documents.

7. The method according to claim 1, wherein the using, by the computer processor system, an iterative process, including a sequence of steps, to select, from said sup-group of documents, a set of documents that establish all the premises of the logical proof includes determining a plurality of sets of documents using theorem proving for scoring the candidate answer.

8. The method according to claim 7, wherein:
the identifying a logical proof of the candidate answer includes identifying a plurality of logical proofs of the candidate answer; and
the determining a plurality of sets of documents using theorem proving for scoring the candidate answer includes using each of the plurality of logical proofs of the candidate answer to determine a respective one of the plurality of sets of documents.

9. The method according to claim 7, wherein the using the set of documents to generate a score for the candidate answer includes selecting one of the plurality of sets of documents to generate a score for the candidate answer.

10. The method according to claim 1, wherein the selecting for said set of documents a plurality of the documents of the sub-group of documents includes using a defined algorithm to identify a minimal number of the documents of said sub-group of documents to form the set of documents.

11. A computer system for searching through a database of documents for documents to generate a score for a candidate answer to an input query, the computer system comprising:
a memory for storing data; and
one or more processor units operatively connected to the memory to transmit data to and to receive data from the memory, and configured for:
indexing the documents in the database, including
for each of the documents, annotating spans of text in said each document that refer to entities with entity types to form entity annotations, and annotating, by the computer processor system, spans of text in said each document that refer to facts with fact types to form relation annotations,
for each of the annotated spans of text that refers to one of the facts, linking, by the computer processor system, said one of the facts to said each annotation, and
recording in an index, the entities, the facts, the annotations that refer to said entities, and the annotations that refer to said facts;
receiving an input query;
identifying a candidate answer to the input query;
determining a set of the documents in the database using said index and theorem proving for scoring the candidate answer, including:
identifying a logical proof of the candidate answer, the logical proof including a conclusion and a sequence of premises that logically prove the conclusion, including using the candidate answer as the conclusion of the logical proof,
searching through a group of documents to identify a sub-group of documents of the group of documents, each document of the sub-group of documents including one or more of the premises of the logical proof, and wherein each of the premises of the logical proof is included in at least one of the documents of the sub-group of documents;

using an iterative process, including a sequence of steps, to select, from said sub-group of documents, a set of documents that establish all the premises of the logical proof, including at each of the steps of the iterative process, selecting for said set of documents one of the documents that, of the documents of said sub-group of documents, has the largest number of the premises of the logical proof that, at the time of said each step, are not included in any of the documents in the set of documents; and using the set of documents to generate a score for the candidate answer.

12. The computer system according to claim 11, wherein the indexing the documents in the database includes:

determining which of the entity annotations refer to the same fact; and determining which of the relation annotations refer to the same fact.

13. The computer system of claim 11, wherein the using, by the computer processor system, an iterative process further includes recognizing after each of the steps the premises of the logical proof that are not in any of the documents in the set of documents.

14. The computer system according to claim 11, wherein the using the iterative process further includes selecting for said set of documents a first document of said sub-group of documents that, of the documents of said sub-group of documents, has the most of the premises of the logical proof.

15. The computer system according to claim 11, wherein the using the iterative process further includes continuing with the iterative process until each of the premises is included in at least one of the documents of said set of documents.

16. An article of manufacture comprising:

at least one tangible computer readable medium having computer readable program code logic to generate answers to questions, the computer readable program code logic, when executing, performing the following:

indexing the documents in the database, including for each of the documents, annotating spans of text in said each document that refer to entities with entity types to form entity annotations, and annotating, by the computer processor system, spans of text in said each document that refer to facts with fact types to form relation annotations, for each of the annotated spans of text that refers to one of the facts, linking, by the computer processor system, said one of the facts to said each annotation, and recording in an index, the entities, the facts, the annotations that refer to said entities, and the annotations that refer to said facts;

receiving an input query at a computer processor system;

identifying, by the computer processor system, a candidate answer to the input query;

determining a set of the documents in the database using said index and theorem proving for scoring the candidate answer, including:

identifying, by the computer processor system, a logical proof of the candidate answer, the logical proof including a conclusion and a sequence of premises that logically prove the conclusion, including using the candidate answer as the conclusion of the logical proof, searching, by the computer processor system, through a group of documents to identify a sub-group of documents of the group of documents, each document of the sub-group of documents including one or more of the premises of the logical proof, and wherein each of the premises of the logical proof is included in at least one of the documents of the sub-group of documents;

using, by the computer processor system, an iterative process, including a sequence of steps, to select, from said sup-group of documents, a set of documents that establish all the premises of the logical proof, including at each of the steps of the iterative process, selecting for said set of documents one of the documents that, of the documents of said sub-group of documents, has the largest number of the premises of the logical proof that, at the time of said each step, are not included in any of the documents in the set of documents; and using, by the computer processor system, the set of documents to generate a score for the candidate answer.

17. The article of manufacture of claim 16, wherein the using, by the computer processor system, an iterative process further includes recognizing after each of the steps the premises of the logical proof that are not in any of the documents in the set of documents.

18. The article of manufacture according to claim 16, wherein the using the iterative process further includes selecting for said set of documents a first document of said sub-group of documents that, of the documents of said sub-group of documents, has the most of the premises of the logical proof.

19. The article of manufacture according to claim 16, wherein the using the iterative process further includes continuing with the iterative process until each of the premises is included in at least one of the documents of said set of documents.

20. The article of manufacture according to claim 16, wherein the searching through a group of documents to identify a sub-group of documents of the group of documents that include one or more of the premises includes identifying a number of the premises in said each document of said sub-group of documents.

* * * * *